US012702402B2

(12) United States Patent
Magno et al.

(10) Patent No.: US 12,702,402 B2
(45) Date of Patent: Aug. 11, 2026

(54) ELECTRIC OR MANUAL GEARED SUTURING DEVICE

(71) Applicant: GYRUS ACMI, INC., Westborough, MA (US)

(72) Inventors: Joey Magno, Cordova, TN (US); Nikhil M. Murdeshwar, Maple Grove, MN (US); Jordan N. Milford, Bethlehem, PA (US)

(73) Assignee: Gyrus ACMI, Inc., Westborough, MA (US)

( * ) Notice: Subject to any disclaimer, the term of this patent is extended or adjusted under 35 U.S.C. 154(b) by 222 days.

(21) Appl. No.: 18/563,560

(22) PCT Filed: May 20, 2022

(86) PCT No.: PCT/US2022/072458

§ 371 (c)(1),
(2) Date: Nov. 22, 2023

(87) PCT Pub. No.: WO2022/251797

PCT Pub. Date: Dec. 1, 2022

(65) Prior Publication Data

US 2024/0245397 A1 Jul. 25, 2024

Related U.S. Application Data

(60) Provisional application No. 63/202,057, filed on May 25, 2021.

(51) Int. Cl.
*A61B 1/00* (2006.01)
*A61B 1/015* (2006.01)
(Continued)

(52) U.S. Cl.
CPC ...... *A61B 17/0469* (2013.01); *A61B 1/00087* (2013.01); *A61B 1/00101* (2013.01);
(Continued)

(58) Field of Classification Search
CPC . A61B 17/0469; A61B 17/29; A61B 17/0483; A61B 17/06119; A61B 17/0491;
(Continued)

(56) References Cited

U.S. PATENT DOCUMENTS 3,817,635 A * 6/1974 Kawahara .......... A61B 1/00165 356/11
5,097,838 A * 3/1992 Hirooka ................. A61B 8/445 600/463

(Continued)

FOREIGN PATENT DOCUMENTS

CN 103118605 5/2013
CN 103298414 9/2013

(Continued)

OTHER PUBLICATIONS

"International Application Serial No. PCT US2022 072458, International Preliminary Report on Patentability mailed Dec. 7, 2023", 10 pgs.

(Continued)

*Primary Examiner* — Anh Tuan T Nguyen
*Assistant Examiner* — James Edward Boice
(74) *Attorney, Agent, or Firm* — Schwegman Lundberg & Woessner, P.A.

(57) ABSTRACT

A suturing system for a scope having a scope shaft comprises a drive shaft to extend along the scope shaft, a mounting ring to mount to a distal end of the scope shaft to receive the drive shaft, a pinion gear mounted to a distal end of the drive shaft, a ring gear rotatably mounted to the mounting ring in engagement with the pinion gear, and a needle mounted to the ring gear.

19 Claims, 23 Drawing Sheets

(51) Int. Cl.
*A61B 1/018* (2006.01)
*A61B 17/04* (2006.01)
*A61B 17/29* (2006.01)

(52) U.S. Cl.
CPC .......... *A61B 1/00133* (2013.01); *A61B 1/015* (2013.01); *A61B 1/018* (2013.01); *A61B 17/29* (2013.01); *A61B 2017/0409* (2013.01)

(58) Field of Classification Search
CPC ............ A61B 1/00087; A61B 1/00101; A61B 1/00133; A61B 1/015; A61B 1/018; A61B 1/00–32; A61B 2017/0409; A61B 2017/00292; A61B 25/0662; A61B 10/04; A61B 1/00135
USPC ......... 600/104; 604/264; 606/139, 144, 228, 606/222
See application file for complete search history.

(56) References Cited

U.S. PATENT DOCUMENTS

| | | | | |
|---|---|---|---|---|
| 5,281,237 | A * | 1/1994 | Gimpelson | A61B 17/2909 606/139 |
| 5,460,166 | A * | 10/1995 | Yabe | A61B 1/0052 600/109 |
| 5,653,718 | A | 8/1997 | Yoon | |
| 5,993,467 | A * | 11/1999 | Yoon | A61B 17/0469 606/147 |
| 6,171,316 | B1 * | 1/2001 | Kovac | A61B 17/062 606/205 |
| 2002/0198542 | A1 | 12/2002 | Yamamoto et al. | |
| 2008/0249404 | A1 | 10/2008 | Mikkaichi et al. | |
| 2012/0059395 | A1 | 3/2012 | Kehdy et al. | |
| 2012/0271327 | A1 | 10/2012 | West et al. | |
| 2013/0110107 | A1 * | 5/2013 | Smith | A61B 1/005 606/41 |
| 2013/0267969 | A1 * | 10/2013 | Martin | A61B 17/0491 606/147 |
| 2014/0296771 | A1 * | 10/2014 | Naito | A61B 1/00156 604/19 |
| 2014/0378761 | A1 * | 12/2014 | Zorn | A61B 34/70 600/104 |
| 2017/0119371 | A1 * | 5/2017 | Mims | A61B 17/0482 |
| 2017/0251903 | A1 * | 9/2017 | Natori | A61B 1/00006 |
| 2020/0261228 | A1 | 8/2020 | Guidotti et al. | |
| 2021/0068812 | A1 | 3/2021 | Favreau et al. | |

FOREIGN PATENT DOCUMENTS

| | | | |
|---|---|---|---|
| CN | 117412714 | | 1/2024 |
| DE | 112022002760 | | 3/2024 |
| JP | 2003038495 | | 2/2003 |
| JP | 2014519880 | | 8/2014 |
| JP | 7787206 | B2 | 12/2025 |
| WO | WO-2018132081 | A1 | 7/2018 |
| WO | WO-2022251797 | A1 | 12/2022 |

OTHER PUBLICATIONS

"Japanese Application Serial No. 2023-572899, Notification of Reasons for Refusal mailed Sep. 30, 2024", W English Translation, 7 pgs.

"Japanese Application Serial No. 2023-572899, Response filed Mar. 31, 2025 to Notification of Reasons for Refusal mailed Sep. 30, 2024", W English Claims, 10 pgs.

"Japanese Application Serial No. 2023-572899, Examiners Decision of Final Refusal mailed May 27, 2025", W English Translation, 4 pgs.

"International Application Serial No. PCT/US2022/072458, International Search Report mailed Sep. 20, 2022", 6 pgs.

"International Application Serial No. PCT/US2022/072458, Written Opinion mailed Sep. 20, 2022", 8 pgs.

"Japanese Application Serial No. 2023-572899, Response filed Sep. 26, 2025 to Examiners Decision of Final Refusal mailed May 27, 2025", w/ english claims, 12 pgs.

"Chinese Application Serial No. 202280037902.5, Office Action mailed Apr. 16, 2026", w English Translation, 13 pgs.

* cited by examiner

ELECTRIC OR MANUAL GEARED SUTURING DEVICE

CLAIM OF PRIORITY

This patent application is a U.S. National Stage filing under 37 U.S.C. § 371 from International Application No. PCT/US2022/072458 to Magno et al., entitled "Electric or Manual Geared Suturing Device," filed on May 20, 2022, which claims the benefit of priority of U.S. Provisional Patent Application Ser. No. 63/202,057 to Magno et al., entitled "Electric or Manual Geared Suturing Device," filed on May 25, 2021, which are hereby incorporated by reference herein in their entireties.

TECHNICAL FIELD

The present disclosure relates generally to medical devices comprising elongate bodies configured to be inserted into incisions or openings in anatomy of a patient to provide diagnostic or treatment operations.

More specifically, the present disclosure relates to medical devices, such as endoscopes, laparoscopes and other scopes, that can be inserted into anatomy of a patient, with or without the aid of another device, to facilitate performance of a medical procedure, such as by cutting, cauterizing or collecting tissue with a forceps.

BACKGROUND

Endoscopes can be used for one or more of 1) providing passage of other devices, e.g., therapeutic devices or tissue collection devices, toward various anatomical portions, and 2) imaging of such anatomical portions. Such anatomical portions can include gastrointestinal tract (e.g., esophagus, stomach, duodenum, pancreaticobiliary duct, intestines, colon, etc.), renal area (e.g., kidney(s), ureter, bladder, urethra, etc.), other internal organs (e.g., reproductive systems, sinus cavities, submucosal regions, respiratory tract), and the like.

Conventional endoscopes can be involved in a variety of clinical procedures, including, for example, illuminating, imaging, detecting and diagnosing one or more disease states, providing fluid delivery (e.g., saline or other preparations via a fluid channel) toward an anatomical region, providing passage (e.g., via a working channel) of one or more therapeutic devices for sampling or treating an anatomical region, and providing suction passageways for collecting fluids (e.g., saline or other preparations) and the like.

In conventional endoscopy, the distal portion of the endoscope can be configured for supporting and orienting a therapeutic device, such as with the use of an elevator. In some systems, two endoscopes can be configured to work together with a first endoscope guiding a second endoscope inserted therein with the aid of the elevator. Such systems can be helpful in guiding endoscopes to anatomic locations within the body that are difficult to reach. For example, some anatomic locations can only be accessed with an endoscope after insertion through a circuitous path.

In view of the foregoing, medical procedures using scopes can involve time and skill to deliver the desired instrument to target anatomy where the instrument is to be used. Furthermore, many decisions must be made pre-operatively as to which instruments are to be used, how the scope is going to be delivered to the target anatomy, and which procedures will be performed on the target anatomy once it is delivered.

SUMMARY

The present inventors have recognized that problems to be solved with conventional medical devices, and in particular medical scopes, such as endoscopes and laparoscopes, used to treat and retrieve biological matter or perform other procedures, include, among other things, 1) the difficulty in navigating endoscopes, and instruments inserted therein, to locations within anatomical regions of a patient, 2) the difficulty of having to decide pre-operatively, before a scope is inserted into anatomy, which instruments are going to be used to perform the procedure without a) seeing the actual anatomy, b) knowing how the procedure actually progresses, and 3) the increased time and associated cost of having to remove and reinsert instruments into the anatomy to perform different procedures, such as tissue collection and suturing, particularly if the pre-operative decisions turn out to be ineffectual.

The present inventors have recognized that such problems can be particularly present in colonoscopy procedures, bariatric producers, and the like. In a colonoscopy procedure, a colonoscope is inserted into the patient to remove diseased tissue, such as polyps, from a colon. This typically involves removing mucosa from surfaces of the gastrointestinal tract. However, sometimes the tissue separation device, e.g., forceps, can puncture through a duct wall of the gastrointestinal tract. If the puncture is severe, it can be desirable to close the puncture, such as with suturing. However, suturing the puncture shut requires the introduction of a suturing device into the anatomy. Typical suturing devices involve dedicated suturing scopes or attachments that couple to the distal end of a scope. In the case of the latter, it can be undesirable to attach these devices before the endoscope is inserted into the anatomy because such devices can be cumbersome, can make the underlying procedure more difficult to perform, and likely will not be needed. As such, in either case, the endoscope must be withdrawn from the patient so that same instrument with the suturing attachment or another instrument can be inserted back into the patient to perform the suturing.

The present disclosure can help provide solutions to these and other problems by providing systems, devices and methods relating to endoscopy procedures to provide 1) a reinsertion sheath that can facilitate withdrawal of an endoscope from anatomy and reinsertion of the endoscope into the same anatomy without having to re-navigate the endoscope and 2) an attachable suturing device that can a) be simple to operate, b) be easily navigated when attached to a scope, c) minimize interference with performance of an underlying endoscope, and d) provide efficient and powerful suturing.

In an example, a suturing system for coupling to a scope having a scope shaft can comprise a drive shaft configured to extend along the scope shaft, a mounting ring configured to mount to a distal end of the scope shaft to receive the drive shaft, a pinion gear mounted to a distal end of the drive shaft, a ring gear rotatably mounted to the mounting ring in engagement with the pinion gear, and a needle mounted to the ring gear.

In another example, a method can comprise coupling a suturing device to a distal end portion of a shaft of an endoscope, rotating a drive shaft extending along the shaft to the suturing device, rotating a suturing element with the drive shaft, moving the suturing element to grasp a suture anchor connected to suturing material, pulling the suturing material with the suturing element, bringing tissue into alignment with the suturing element, and pushing the suture anchor and the suturing material through the tissue.

In additional examples, the present disclosure relates to a suturing device that can be attached to a distal end of a medical scope, such as an endoscope that includes various imaging and navigation features. Example endoscopes include a camera, a light emitter and one or more working channels through which other instruments and capabilities, such as irrigation or suction, can be delivered. Operational aspects of such features are typically located on a distal end face of a shaft of the scope.

In the present disclosure, a suturing device can be attached to a distal end portion of the shaft of the scope to provide suturing capabilities to the endoscope. The suturing device can include a shaft that can be driven from a proximal end. In examples, the shaft can be driven by an electric motor and/or via a manually operated crank. A distal end of the shaft can be used to rotate or reciprocate a suturing element, such as via a gearing system. In examples, the shaft can include a pinion gear. A coupling element, such as a coupling ring, can be configured to mount a drive gear to the shaft of the scope that provides input to the suturing element. In examples, the drive gear can comprise a ring gear having internal gear teeth configured to mate with external gear teeth of the pinion gear. In examples, the drive gear can comprise a ring hear having external teeth configured to mate with external gear teeth of the pinion gear. In examples, the drive gear can comprise a ring gear having internal and external gear teeth to mate with the pinion gear and an offsetting gear. In examples, the coupling element can comprise a ring configured to be centered on the distal end face of the shaft of a scope to mount components within the area of the distal end face. In examples, the coupling element can comprise a ring configured to mount components within the area of the distal end face and outside of the area of the distal end face. As such, the shaft can be rotated via electrical or manual power to rotate a pinion gear that rotates a ring gear from which a suturing element extends to thread suturing material.

In examples, suturing material can be extended through a first working channel to connect to the suturing element. The first working channel can be located in the shaft of the endoscope or can be provided via external elements extending alongside the shaft, such as a tube.

In examples, means for bringing tissue into engagement with the suturing element can be incorporated into the suturing device. In examples, suction can be provided to pull tissue into the path of the suturing element. In examples, the suction can be provided through a second working channel connected to a suction source. In examples, a forceps can be used to bring the tissue into the path of the suturing element. The second working channel can be located in the shaft of the endoscope or can be provided via external elements extending alongside the shaft, such as a tube.

In examples, such as those shown with reference to FIGS. 14-23, the suturing element can comprise an arcuate needle having a pointed tip and a socket to receive a suture anchor. In examples, the suture anchor can comprise a ball fastened or attached to a distal end of a strand of suturing material. The coupling element can be configured to hold the anchor distal of the first working channel such that rotation of the suturing element can cause the suturing element to pick up and/or drop off the anchor at the coupling element. Thus, as the suturing element rotates with the ring gear the tip of the suturing element can be driven through tissue while simultaneously carrying the anchor and the distal end of the suturing material through the tissue from a first side of the tissue to a second side of the tissue. The suturing element can be contra-rotated to withdraw the tip if the suturing element from the tissue, leaving the anchor in place on the second side of the tissue. The anchor can be positioned back in the coupling element. The suturing device can then be repositioned to a different location on the tissue and the process can be repeated.

In examples, the major components are the main housing which comprises the pinion gear that is connected to a flexible shaft where the rotating source is a miniature electric motor that is located remotely outside of the length of the endoscope where it is housed near the endoscope user controls, a needle ring gear that can rotate along the circumference of the main housing through an internal gear that meshes with the pinion gear and a retaining ring that keeps the ring gear with the main housing. The main housing has openings for two working channels where one can be for a miniature forceps or a vacuum tube access port and another for the ball and suture assembly. The main housing may be fitted snugly to the tip of the endoscope and have locating features like a flat side or a pin to align the working channels of the endoscope to the main housing working channels. The tip of the ring gear can have a feature to catch the ball and suture. The ball and suture assembly can have a catch housing for the ball and suture. This ball and suture assembly can be pre-assembled to the main housing by threading into the proximal end of the working channel of the endoscope and once outside at the distal tip, the catch housing can be snapped to the main housing working channel.

DETAILED DESCRIPTION

Figure 1:
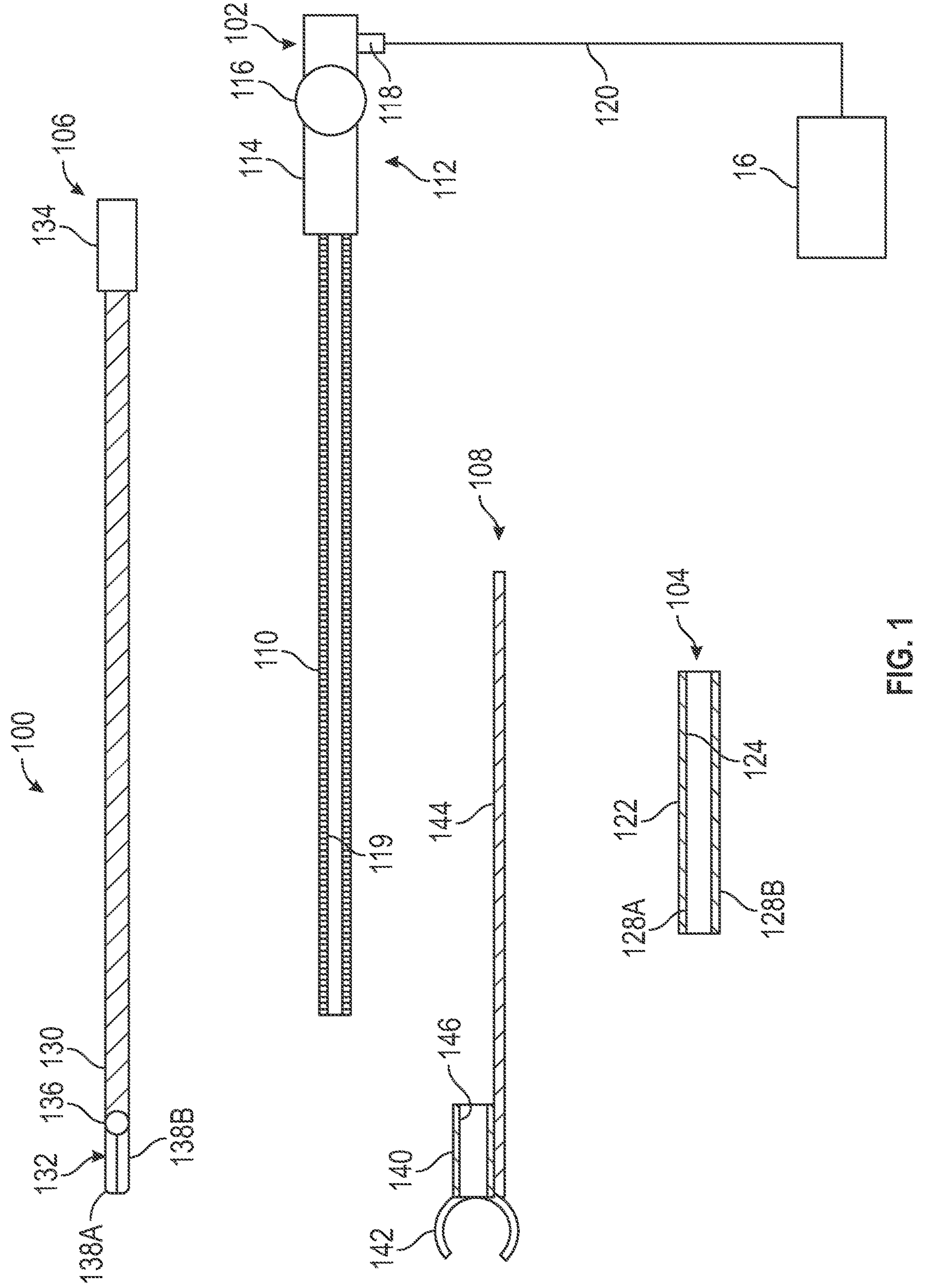
FIG. 1 is a schematic cross-sectional diagram of an endoscope system comprising a scope, a reinsertion sheath, a tissue separator device and a suturing attachment in an exploded configuration showing lumens through the system.
Figure 2:
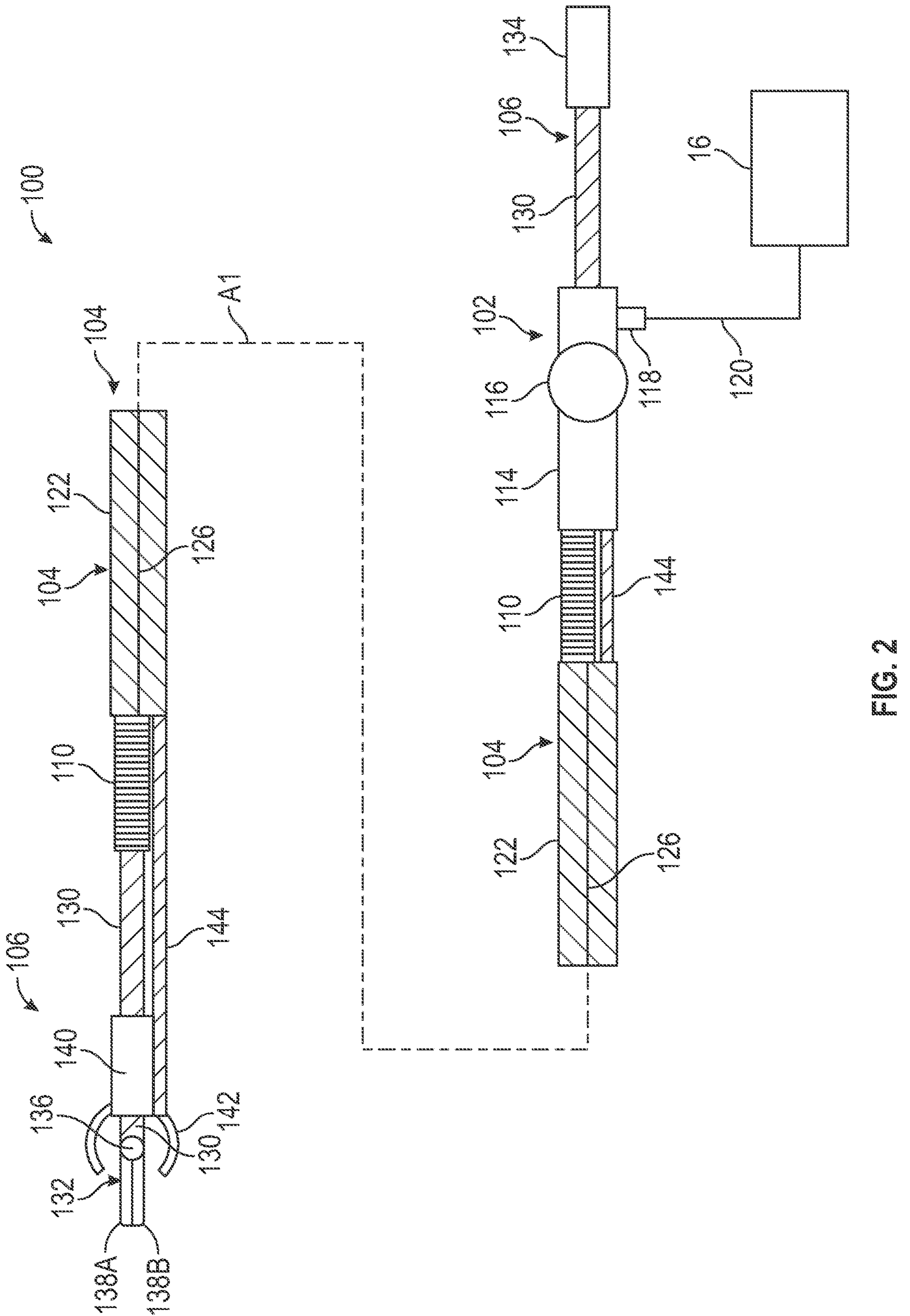
FIG. 2 is a schematic diagram of the endoscope system of FIG. 1 in an assembled state showing the tissue separator device and the suturing attachment positioned at a distal end of the scope, and the reinsertion sheath positioned around the scope.

FIG. 1 is a schematic diagram of endoscope system 100 in an exploded state. FIG. 2 is a schematic diagram of endoscope system 100 of FIG. 1 in an assembled state. FIGS. 1 and 2 are discussed concurrently. FIGS. 1 and 2 are not necessarily drawn to scale and may be exaggerated in certain aspects for illustrative purposes.

System 100 can comprise scope 102, reinsertion sheath 104, tissue separator device 106 and suturing device 108. In FIG. 1, scope 102, reinsertion sheath 104, tissue separator device 106 and suturing device 108 are in a disassembled configuration. In FIG. 2, tissue separator device 106 and suturing device 108 are positioned at a distal end of scope 102, and reinsertion sheath 104 positioned around scope 102.

Scope 102, which is described in greater detail with reference to FIGS. 3-5B, can comprise shaft 110 and controller 112, which can include grip 114, control knob 116 and coupler 118. Shaft 110 can comprise an elongate body including lumen 119. Coupler 118 can connect to control unit 16 (FIG. 4) via cable 120.

Reinsertion sheath 104 can comprise shaft 122 and lumen 124. Shaft 122 can comprise slit 126 (FIG. 2) that forms flanges 128A and 128B.

Tissue separator device 106 can comprise shaft 130, tissue separator 132 and control device 134. Tissue separator 132 can comprise hinge 136 and separators 138A and 138B.

Suturing device 108 can comprise coupler 140, suturing body 142 and control element 144. Coupler 140 can comprise lumen 146.

FIG. 2 shows scope 102 nested inside of sheath 104, tissue separator device 106 nested inside scope 102, and suturing device 108 coupled to the end of scope 102. As such, as can be seen in FIG. 1, reinsertion sheath 104 can comprise lumen 124 and scope 102 can comprise lumen 119.

As is discussed in greater detail herein, endoscopy system 100 can be configured to provide the ability to insert scope 102 with tissue separator device 106 into anatomy and subsequently decide to assemble suturing device 108 to the distal end of scope 102.

Reinsertion sheath 104 can be assembled to shaft 110 of scope 102 while shaft 110 is inserted into the anatomy. Reinsertion sheath 104 can include various features to facilitate assembly with the proximal end of shaft 110. For example, reinsertion sheath 104 can include slit 126 to allow shaft 122 to be slipped onto shaft 110 in a radial direction. Additionally, reinsertion sheath 104 can include axial contraction and expansion capabilities to facilitate the assembly and insertion steps. Thus, scope 102 can be withdrawn from reinsertion sheath 104, assembled with suturing device 108 and reinserted into reinsertion sheath 104, with or without tissue separator device 106.

Scope 102 can be configured as a fully functional endoscope including steerability, guidance capability, imaging capability, fluid dispensing and retrieving capabilities, and functional (e.g., therapeutic and diagnostic) capabilities, as well as a passageway for other instruments. Functionality of scope 102 is described in detail with reference to endoscope 14 of FIGS. 3-5B below and, as such, is only shown schematically in FIGS. 1 and 2.

The term "tissue separator device" is used throughout the present disclosure, however tissue separator device 106 can alternatively or additionally comprise a biological matter collection device, a biological matter retrieval device, a tissue collection device and tissue retrieval device. Tissue separator device 106 can be configured as any suitable device configured to obtain, retrieve, collect and/or remove tissue samples from within a patient. Tissue separator device 106 can comprise a component or device for interacting with a patient, such as those configured to cut, slice, pull, saw, punch, twist or auger tissue, and the like. Specifically, tissue separator device 106 can comprise any device suitable for removing tissue from a patient, such as a blade, punch or an auger. Tissue separator device 106 can be configured to physically separate portions of tissue of a patient from other larger portions of tissue in the patient. In additional examples, tissue separator device 106 can be configured to simply collect biological matter from the patient that does not need physical separation, such as mucus or fluid, that is already or naturally separate or distinct. In the illustrated example, tissue separator device 106 can comprise forceps having separators 138A and 138B configured as sharpened or serrated jaws pivotably connected at hinge 136. Tissue separator device 106 can, however, be configured as a variety of devices capable of collecting biological matter, such as a punch, an auger, a blade, a saw and the like, as mentioned. Tissue separator device 106 can be configured to hold a volume of collected biological matter, e.g., tissue, such as between separators 138A and 138B. As such, tissue separator device 106 can be configured to be withdrawn from scope 102 to obtain the collected biological matter, such as for diagnostic analysis or disposal.

Figure 3:
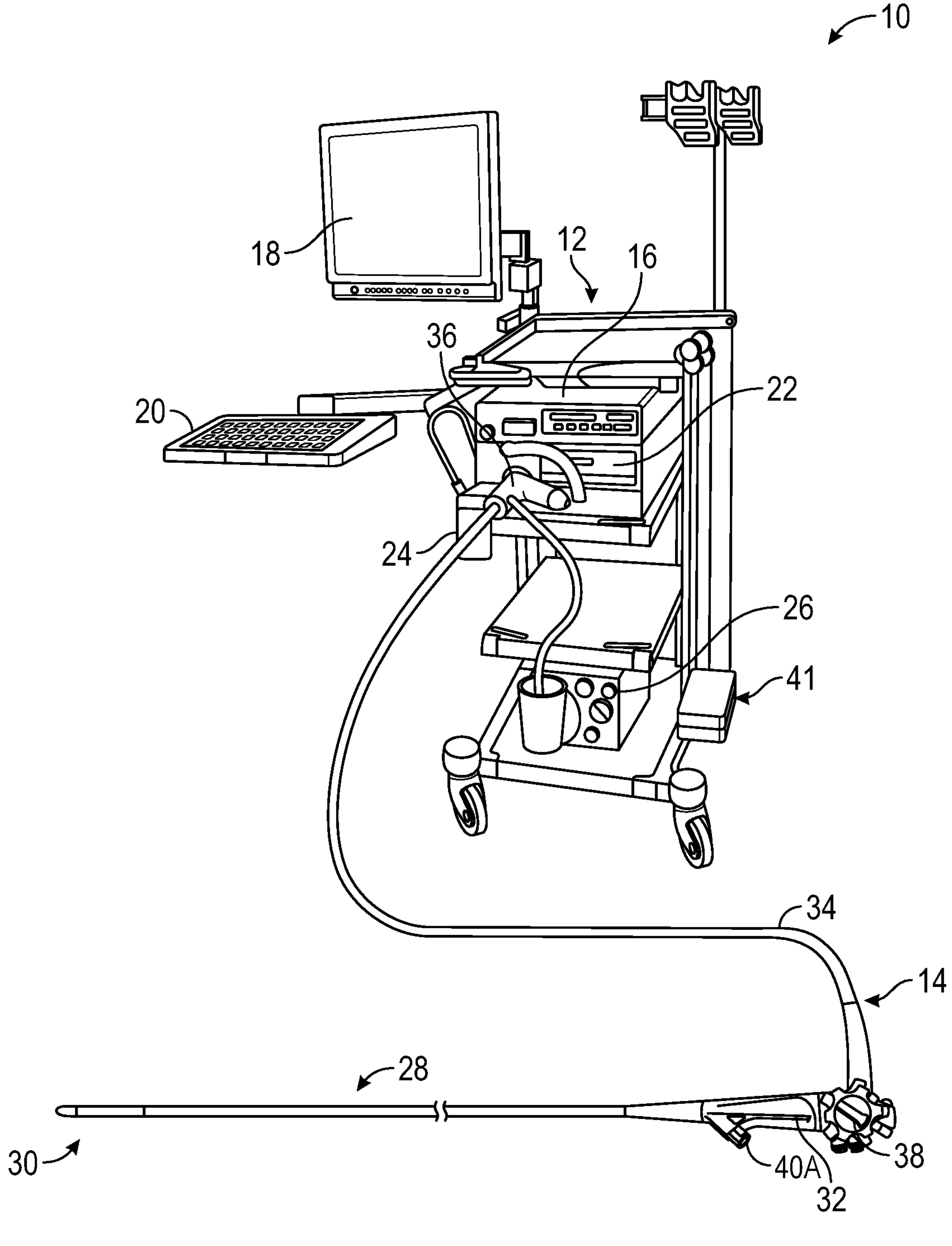
FIG. 3 is a schematic illustration of an imaging and control system comprising a control unit connected to the scope of FIGS. 1 and 2.

FIG. 3 is a schematic diagram of endoscopy system 10 comprising imaging and control system 12 and endoscope 14. The system of FIG. 3 is an illustrative example of an endoscopy system suitable for use with the systems, devices and methods described herein, such as colonoscopy procedures, bariatric producers, and the like, that can be used for removing and obtaining tissue or other biological matter from a patient for analysis or treatment of the patient. According to some examples, endoscope 14 can comprise scope 102 of FIGS. 1 and 2 and can be insertable into an anatomical region for imaging and/or to provide passage of one or more collection devices for biopsies, or one or more therapeutic devices for treatment of a disease state associated with the anatomical region. Endoscope 14 can, in advantageous aspects, interface with and connect to imaging and control system 12. In the illustrated example, endoscope 14 comprises an end-viewing colonoscope, though other types of endoscopes can be used with the features and teachings of the present disclosure.

Imaging and control system 12 can comprise control unit 16, output unit 18, input unit 20, light source unit 22, fluid source 24 and suction pump 26.

Imaging and control system 12 can include various ports for coupling with endoscopy system 10. For example, control unit 16 can include a data input/output port for receiving data from and communicating data to endoscope 14. Light source unit 22 can include an output port for transmitting light to endoscope 14, such as via a fiber optic link. Fluid source 24 can include a port for transmitting fluid to endoscope 14. Fluid source 24 can comprise a pump and a tank of fluid or can be connected to an external tank, vessel or storage unit. Suction pump 26 can comprise a port used to draw a vacuum from endoscope 14 to generate suction, such as for withdrawing fluid from the anatomical region into which endoscope 14 is inserted. Output unit 18 and input unit 20 can be used by an operator of endoscopy system 10 to control functions of endoscopy system 10 and view output of endoscope 14. Control unit 16 can additionally be used to generate signals or other outputs from treating the anatomical region into which endoscope 14 is inserted. In examples, control unit 16 can generate electrical output, acoustic output, a fluid output and the like for treating the anatomical region with, for example, cauterizing, cutting, freezing and the like. Endoscope 14 can comprise insertion section 28, functional section 30 and handle section 32, which can be coupled to cable section 34 and coupler section 36. Coupler section 36 can be connected to control unit 16 to connect to endoscope 14 to multiple features of control unit 16, such as input unit 20, light source unit 22, fluid source 24 and suction pump 26.

Insertion section 28 can extend distally from handle section 32 and cable section 34 can extend proximally from handle section 32. Insertion section 28 can be elongate and include a bending section, and a distal end to which functional section 30 can be attached. The bending section can be controllable (e.g., by pull wires connected to control knob 38 on handle section 32) to maneuver the distal end through tortuous anatomical passageways (e.g., stomach, duodenum, kidney, ureter, colon, etc.). Insertion section 28 can also include one or more working channels (e.g., an internal lumen) that can be elongate and support insertion of one or more therapeutic tools of functional section 30, such as tissue separator device 106 of FIGS. 1 and 2. The working channel can extend between handle section 32 and functional section 30. Additional functionalities, such as fluid passages, guide wires, and pull wires can also be provided by insertion section 28 (e.g., via suction or irrigation passageways, and the like).

Handle section 32 can comprise knob 38 as well as port 40A. Knob 38 can be coupled to a pull wire, or other actuation mechanisms, extending through insertion section 28. Port 40A, as well as other ports, such as port 40B (FIG. 2), can be configured to couple various electrical cables, guide wires, auxiliary scopes, tissue collection devices, fluid tubes and the like to handle section 32 for coupling with insertion section 28. For example, tissue separator device 106 can be fed into endoscope 14 via port 40A.

Imaging and control system 12, according to examples, can be provided on a mobile platform (e.g., cart 41) with shelves for housing light source unit 22, suction pump 26, image processing unit 42 (FIG. 4), etc. Alternatively, several components of imaging and control system 12 shown in FIGS. 3 and 4 can be provided directly on endoscope 14 so as to make the endoscope "self-contained."

Functional section 30 can comprise components for treating and diagnosing anatomy of a patient. Functional section 30 can comprise an imaging device, an illumination device and an elevator. Functional section 30 can comprise imaging and illuminating components configured for end-viewing, e.g., viewing distally or axially beyond of functional section 30, such as is described further with reference to camera module 70 of FIGS. 5A and 5B.

Figure 4:
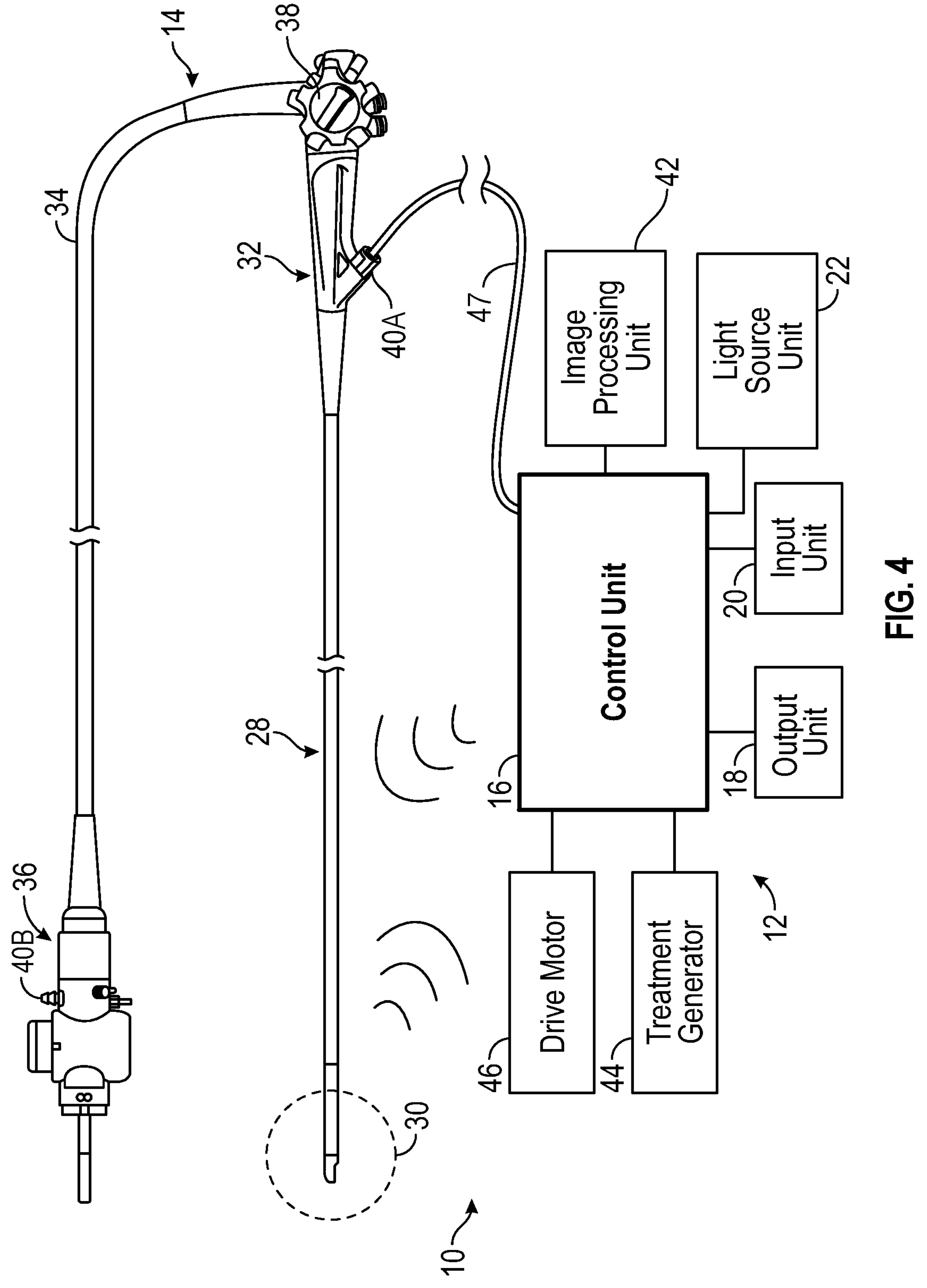
FIG. 4 is schematic diagram of the control unit of FIG. 3 connected to the scope.

FIG. 4 is a schematic diagram of endoscopy system 10 of FIG. 3 comprising imaging and control system 12 and endoscope 14. FIG. 4 schematically illustrates components of imaging and control system 12 coupled to endoscope 14, which in the illustrated example comprises an end-viewing colonoscope. Imaging and control system 12 can comprise control unit 16, which can include or be coupled to image processing unit 42, treatment generator 44 and drive unit 46, as well as light source unit 22, input unit 20 and output unit 18. Coupler section 36 can be connected to control unit 16 to connect to endoscope 14 to multiple features of control unit 16, such as image processing unit 42 and treatment generator 44. In examples, port 40A can be used to insert another instrument or device, such as a daughter scope or auxiliary scope, into endoscope 14. Such instruments and devices can be independently connected to control unit 16 via cable 47. In examples, port 40B can be used to connect coupler section 36 to various inputs and outputs, such as video, air, light and electric. As is discussed below in greater detail with reference to FIGS. 14-23, control unit 16 can comprise, or can be in communication with, devices for implanting or inserting suture material into tissue, such as suturing device 302 of FIG. 14, suturing device 502 of FIGS. 15-21F, suturing device 600 of FIG. 22 and suturing device 650 of FIG. 23. Control unit 16 can be configured to activate a camera to view target tissue distal of endoscope 14. Likewise, control unit 16 can be configured to activate light source unit 22 to shine light on surgical instruments extending from endoscope 14.

Image processing unit 42 and light source unit 22 can each interface with endoscope 14 (e.g., at functional section 30) by wired or wireless electrical connections. Imaging and control system 12 can accordingly illuminate an anatomical region, collect signals representing the anatomical region, process signals representing the anatomical region, and display images representing the anatomical region on output unit 18, which can comprise a cathode ray tube, an LCD display, an LED display and other graphical user interfaces. Imaging and control system 12 can include light source unit 22 to illuminate the anatomical region using light of desired spectrum (e.g., broadband white light, narrow-band imaging using preferred electromagnetic wavelengths, and the like). Imaging and control system 12 can connect (e.g., via an endoscope connector) to endoscope 14 for signal transmission (e.g., light output from light source, video signals from imaging system in the distal end, diagnostic and sensor signals from a diagnostic device, and the like).

Fluid source 24 (FIG. 1) can be in communication with control unit 16 and can comprise one or more sources of air, saline or other fluids, as well as associated fluid pathways (e.g., air channels, irrigation channels, suction channels) and connectors (barb fittings, fluid seals, valves and the like). Imaging and control system 12 can also include drive unit 46, which can be an optional component. Drive unit 46 can comprise a motorized drive for advancing a distal section of endoscope 14, as described in at least PCT Pub. No. WO 2011/140118 A1 to Frassica et al., titled "Rotate-to-Advance Catheterization System," which is hereby incorporated in its entirety by this reference.

Figure 5B:
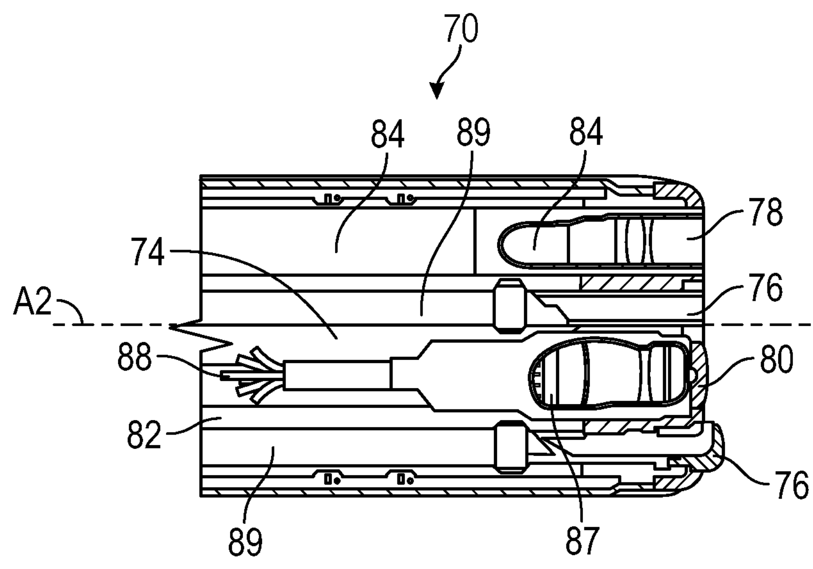
FIG. 5B is a cross-sectional view taken along section 5B-5B of FIG. 5A showing components of the camera module.
Figure 5A:
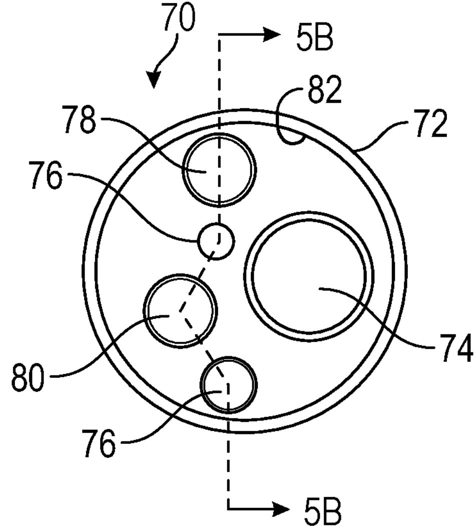
FIG. 5A is an end view of a camera module including optical and functional components suitable for use with the scope of FIGS. 1-4.

FIGS. 5A and 5B illustrate an example of functional section 30 of endoscope 14 of FIG. 4. FIG. 5A illustrates an end view of functional section 30 and FIG. 5B illustrates a cross-sectional view of functional section 30 taken along section plane 5B-5B of FIG. 5A. FIGS. 5A and 5B each illustrate "end-viewing endoscope" (e.g., gastroscope, colonoscope, cholangioscope, etc.) camera module 70. In end-viewing endoscope camera module 70, illumination and imaging systems are positioned such that the viewing angle of the imaging system corresponds to a target anatomy located adjacent (e.g., distal of) an end of endoscope 14 and in line with central longitudinal axis A1 of endoscope 14.

In the example of FIGS. 5A and 5B, end-viewing endoscope camera module 70 can comprise housing 72, working channel 74, fluid outlets 76, illumination lens 78 and objective lens 80. Housing 72 can comprise and endcap for insertion section 28, thereby providing a seal to lumen 82.

As can be seen in FIG. 5B, insertion section 28 can comprise lumen 82 through which various components can be extended to connect functional section 30 with handle section 32 (FIG. 4). For example, illumination lens 78 can be connected to light transmitter 84, which can comprise a fiber optic cable or cable bundle extending to light source unit 22 (FIG. 4). Likewise, objective lens 80 can be coupled to imaging unit 87, which can be coupled to wiring 88. Also, fluid outlets 76 can be coupled to fluid lines 89, which can comprise a tube extending to fluid source 24 (FIG. 4). In examples, one of fluid outlets 76 can comprise an inlet connected to a fluid line 89 configured for suction, such as being connected to a vacuum, for recovery of lavage and irrigation fluid. Other elongate elements, e.g., tubes, wires, cables, can extend through lumen 82 to connect functional section 30 with components of endoscopy system 10, such as suction pump 26 (FIG. 4) and treatment generator 44 (FIG. 4). For example, working channel 74 can comprise a wide-diameter lumen for receiving other treatment components, such as cutting devices and therapeutic devices including tissue separator device 106.

Endoscope camera module 70 can also include a photosensitive element, such as a charge-coupled device ("CCD" sensor) or a complementary metal-oxide semiconductor ("CMOS") sensor. In either example, imaging unit 87 can be coupled (e.g., via wired or wireless connections) to image processing unit 42 (FIG. 4) to transmit signals from the photosensitive element representing images (e.g., video signals) to image processing unit 42, in turn to be displayed on a display such as output unit 18. In various examples, imaging and control system 12 and imaging unit 87 can be configured to provide outputs at desired resolution (e.g., at least 480p, at least 720p, at least 1080p, at least 4K UHD, etc.) suitable for endoscopy procedures.

As described herein, working channel 74 can be used to deliver tissue separator device 106 to target tissue. Additionally, suturing device 108 can be positioned over the distal end portion of housing 72 to provide suturing functionality distal of illumination lens 78 and objective lens 80. Furthermore, reinsertion sheath 104 can be positioned around insertion section 28 proximal of housing 72 to allow endoscope 14 to be inserted into and withdrawn from anatomy without any or with minimal steering and navigation.

Figures 6, 7, 8A, 8B:
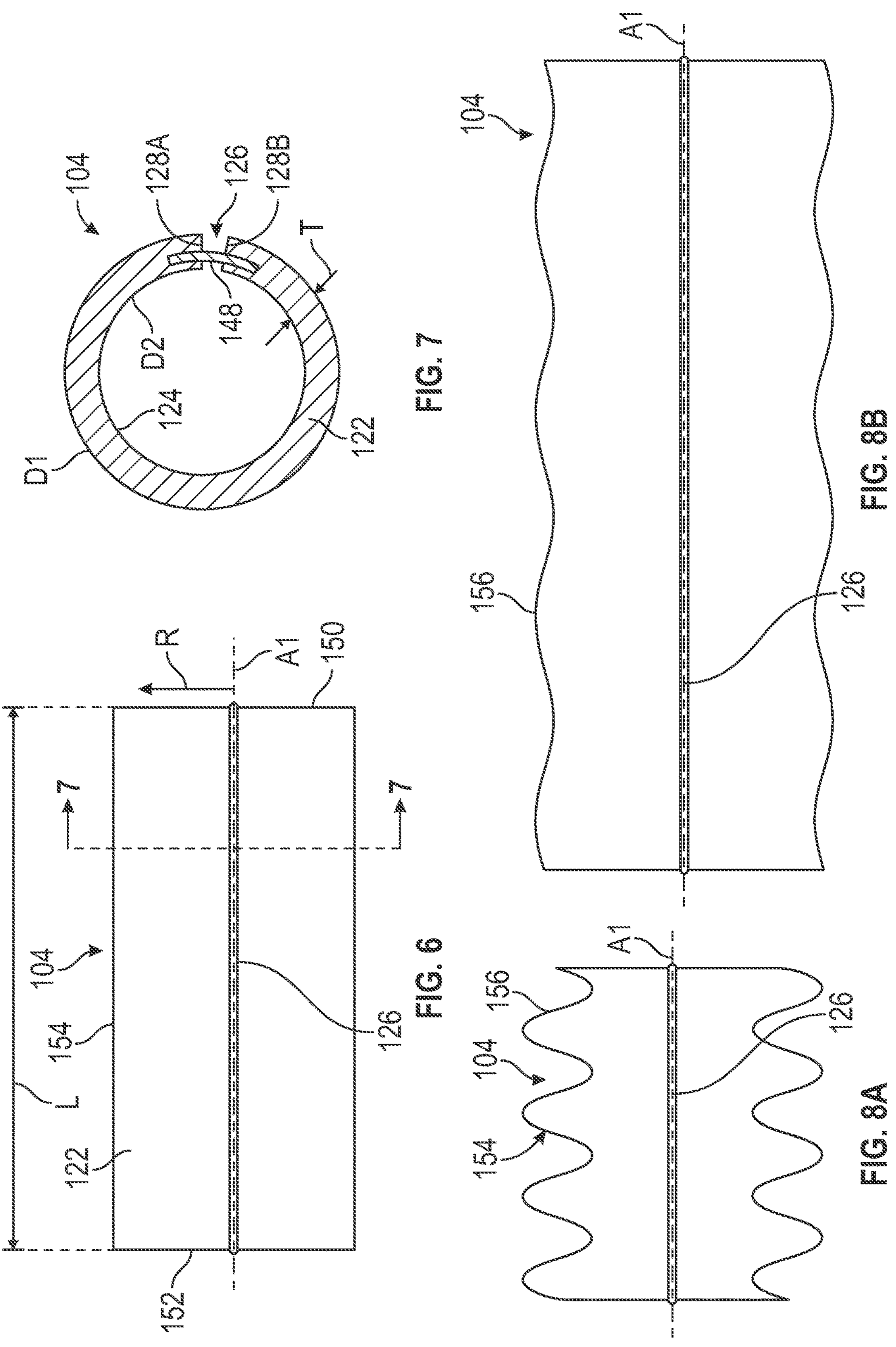
FIG. 6 is a schematic side view of a reinsertion sheath of the present disclosure showing a slit in skin of a shaft.
FIG. 7 is a schematic cross-sectional view taken along section 7-7 of FIG. 6 showing an internal lumen of the reinsertion sheath.
FIG. 8A is schematic side view of the reinsertion sheath of FIG. 6 in a compressed state such that the skin is corrugated.
FIG. 8B is a schematic side view of the reinsertion sheath of FIG. 8A in an extended state such that the skin is expanded.

FIG. 6 is a schematic side view of reinsertion sheath 104 of the present disclosure showing slit 126 in shaft 122. FIG. 7 is a schematic cross-sectional view of reinsertion sheath 104 of FIG. 6 showing internal lumen 124 extending within shaft 122. Shaft 122 can include slit 126 that forms flanges 128A and 128B. In examples, shaft 122 can further comprise rotating door 148. FIGS. 6 and 7 are discussed concurrently.

Shaft 122 can extend axially from first, proximal end 150 to second, distal end 152 along axis A1. In the illustrated example, flanges 128A and 128B can form end faces that are separated by a distance. In other examples, flanges 128A and 128B can contact each other to form a continuous three-hundred-sixty-degree perimeter. In examples, rotatable door 148 can extend from a channel in on of flanges 128A into a channel in another of flanges 128B. Rotatable door 148 can be opened to allow for a scope to be positioned inside lumen 124 and then can be rotated closed to secure the scope therein.

Lumen 124 can extend between proximal end 150 and distal end 152. Lumen 124 can extend from axis A1 in radial direction R. Walls of shaft 122 can have thickness T. The outer diameter D1 of shaft 122 can be configured to fit into a desired anatomy. Inner diameter D2 of shaft 122 can be sized to fit around shaft 110 of scope 102 (FIGS. 1 and 2). Shaft 122 is illustrated as having length L, which, as shown in FIGS. 8A and 8B, can be compacted and expanded as desired in various examples. Shaft 122 is not drawn to scale in FIG. 6 and thus can be longer in direction L than illustrated.

Shaft 122 can be fabricated from any suitable biocompatible material. In examples, shaft 122 can be made of a polymer material. The material of shaft 122 can allow for reinsertion sheath 104 to be deformed via manipulation by an operator, such as a surgeon. For example, an operator of reinsertion sheath 104 can pull flanges 128A and 128B apart to allow scope 102 (FIG. 1) to be positioned inside lumen 124. However, when deployed in anatomy, reinsertion sheath 104 can be configured to retain rigidity to displace anatomy and guide an instrument through lumen 124. Thickness T can be selected to allow shaft 122 to be contracted or crumpled, as shown in FIG. 8A, but extended to provide the desired passageway through anatomy. Thus, thickness T can be selected to allow an operator to manually contract or extend length L, but once extended shaft 122 can be configured to maintain shape.

FIG. 6 is intended to illustrate the fully extended length of shaft 122 at rest when not subject to any compressive or tensile loading such that the outer surface 154 is approximately straight. However, shaft 122 can be subject to compressive forces to reduce length L, as shown in FIG. 8A.

FIG. 8A is schematic side view of reinsertion sheath 104 of FIGS. 6 and 7 in a compressed state. Reinsertion sheath 104 can be compressed along axis A1 to the corrugated state of FIG. 8A. Outer surface 154 of reinsertion sheath 104 can be become compressed to form undulations 156 as the material of shaft 122 becomes furrowed.

FIG. 8B is a schematic side view of reinsertion sheath 104 of FIG. 8A in an extended state along axis A1. As such, undulations 156 can become muted as shaft 122 becomes furrowed. In examples, reinsertion sheath 104 can be fabricated from a rigid corrugated plastic having radially extending rigid portions connected by living hinges such that the reinsertion sheath can be selectively extended and bent is desired orientations.

In examples, the material of shaft 122 can be compliant to allow sheath 104 to be expanded and contracted in the radial direction along axis A1. The material of shaft 122 can comprise a flexible polymeric sheet reinforced with webbing, such as a ripstop material. In order to provide radial stiffness to sheath 104, shaft 122 can be provided with various stiffening means to retain the desired outer diameter of sheath 104, as discussed with reference to FIGS. 9A-10B.

Figures 9A, 9B, 10A, 10B:
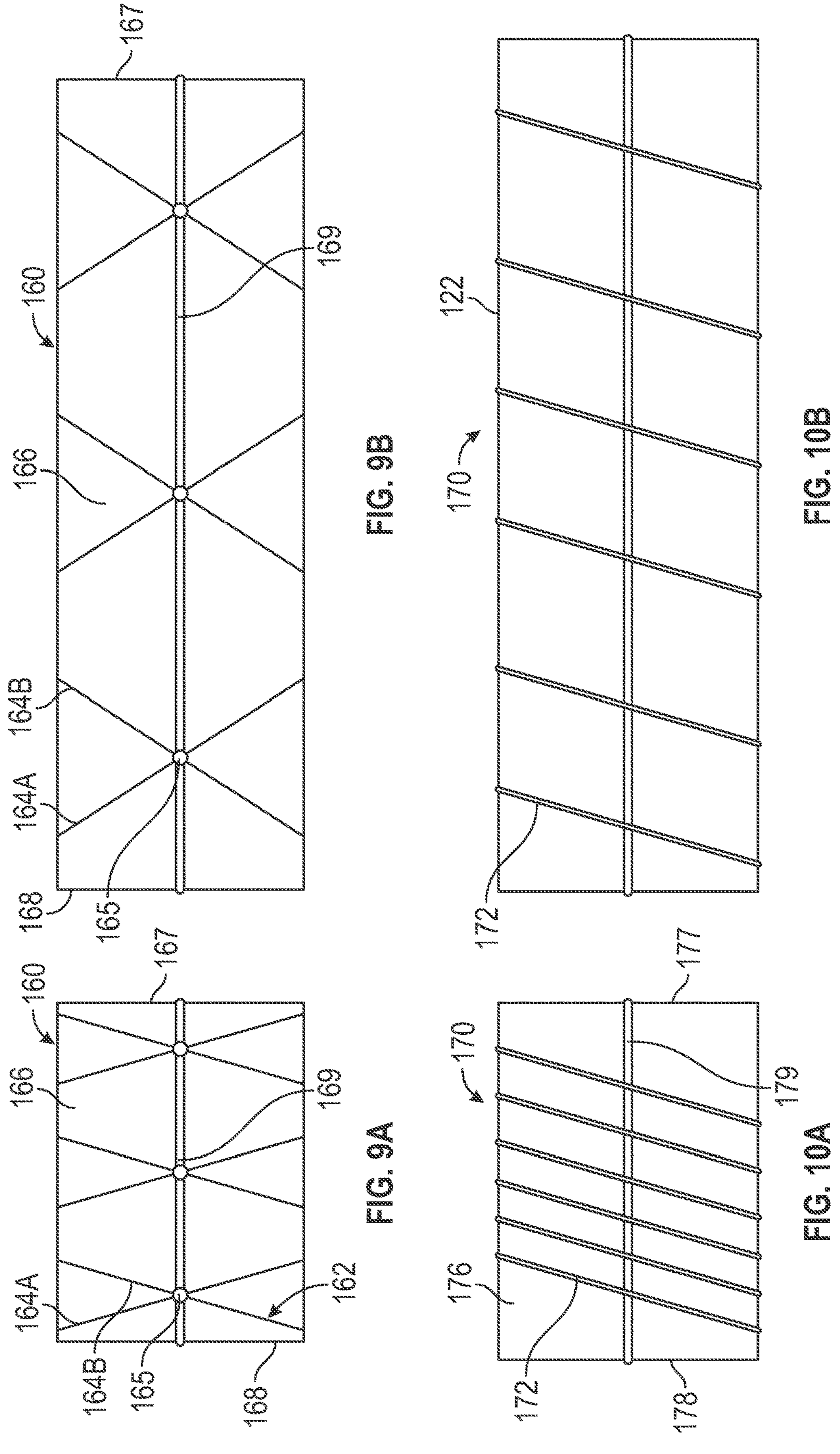
FIG. 9A is a schematic side view of the reinsertion sheath of FIG. 6 having expandable supports in a compressed state.
FIG. 9B is a schematic side view of the reinsertion sheath of FIG. 9A in an extended state.
FIG. 10A is a schematic side view of the reinsertion sheath of FIG. 6 having a helical support member in a compressed state.
FIG. 10B is a schematic side view of the reinsertion sheath of FIG. 10A in an extended state.

FIG. 9A is a schematic side view of reinsertion sheath 160 having expandable supports 162 in a contracted state. FIG. 9B is a schematic side view of reinsertion sheath 160 of FIG. 9A in an extended state. FIGS. 9A and 9B are discussed concurrently.

Reinsertion sheath 160 can be constructed similarly to reinsertion sheath 104 of FIGS. 6-8B with the addition of cross-supports or struts 164A and 164B. Reinsertion sheath 160 can comprise expandable supports 162 attached to body 166, which can extend from first end 167 to second end 168. Expandable supports 162 can comprise struts 164A and 164B that can be connected at hinges 165. Slit 169 can extend across body 166. Slit 169 is schematically illustrated as extending along body 166. Slit 169 can be positioned on body 166 on an opposite side as expandable supports 162. As such, when viewed from an end of reinsertion sheath 160, such as the view of FIG. 7, struts 164A and 164B can have a C-shape with slit 169 forming the ends of the C.

Struts 164A and 164B can comprise wires or bars embedded in or attached to the material of body 166 inside or outside of lumen 124. Struts 164A and 164B can comprise rigid or stiff members to support the material of body 166 in the radial and circumferential directions relative to axis A1. Hinges 165 can comprise pivot points to allow struts 164A and 164B to rotate relative to each other while maintaining contact to provide radial and circumferential support to body 166. Struts 164A and 164B can be configured to minimally impact the axial rigidity of reinsertion sheath 160.

Body 166 can provide a skin over expandable supports 162 to provide a shaft structure. The skin can comprise a flexible polymeric sheet reinforced with webbing, such as a ripstop material. Body 166 can be configured to provide the desired axial stiffness to reinsertion sheath 160.

FIG. 9A shows struts 164A and 164B in a collapsed state where ends of struts 164A and 164B are closer together. However, as can be seen in FIG. 9B, struts 164A and 164B can be opened by rotation at hinges 165 as reinsertion sheath 160 is expanded such that ends 167 and 168 are further apart as compared to FIG. 9A.

Thus, body 166 of reinsertion sheath 160 can be compressed with struts 164A and 164B rotated at hinges 165 to the state of FIG. 9A to facilitate assembly with a scope. When it is desired that reinsertion sheath 160 be deployed, an operator can pull body 166 apart in the circumferential direction at slit 169 to allow sheath 160 to be positioned over shaft 110 of scope 102. In particular, collapsed reinsertion sheath 160 can be positioned over a proximal end of shaft 110 while a distal end of shaft 110 is positioned in anatomy of a patient. Once positioned over shaft 110, an operator can push the distal end of reinsertion sheath 160 along shaft 110 into anatomy of the patient. As mentioned, the stiffness of body 166 can be such that the operator can unfurrow body 166 from the collapsed configuration, but as body 166 is incrementally increased in size, body 166 can maintain its own shape under pressure from the anatomy. Struts 164A and 164B can provide radial stiffening to reinsertion sheath 160 to allow body 166 to resist the anatomy and allow other devices and instruments to be inserted therein, such as scope 102 (FIGS. 1 and 2). Thus, the length L (FIG. 6) of reinsertion sheath 160 can be long enough to reach the distal end of scope 102 or close thereto. Once reinsertion sheath 160 is deployed into the anatomy and fully extended or sufficiently extended to reach an end portion of scope 102, scope 102 can be withdrawn and reinsertion sheath 160 can remain. Inner diameter D2 (FIG. 7) can thus provide a body forming a tunnel to the desired anatomy. As such, scope 102 need not be independently navigated back to the anatomy, but can be simply inserted into reinsertion sheath 160 to reach the desired anatomy. Thus, scope 102 can be withdrawn from anatomy through reinsertion sheath 160 to attach one of the suturing devices described herein with reference to FIGS. 14-23 and then reinserted with the suturing device to reach the same anatomy.

FIG. 10A is a schematic side view of reinsertion sheath 170 having helical support member 172 in a contracted state. FIG. 10B is a schematic side view of reinsertion sheath 170 of FIG. 10A in an extended state. FIGS. 10A and 10B are discussed concurrently.

Reinsertion sheath 170 can comprise body 176 extending between ends 177 and 178. Slit 179 can extend along body 176. Reinsertion sheath 170 can be constructed similarly to reinsertion sheath 160 of FIGS. 9A and 9B with expandable supports 162 being replaced with helical support member 172. Helical support member 172 can comprise a rigid or stiff member that spirals along reinsertion sheath 170 between ends 177 and 178.

Slit 179 can extend across body 176. Slit 179 is schematically illustrated as extending along body 176. Slit 179 can be positioned on body 176 on an opposite side as helical support member 172. As such, when viewed from an end of reinsertion sheath 170, such as the view of FIG. 7, helical support member 172 can have a C-shape with slit 169 forming the ends of the C. As such, helical support member 172 may not form a continuous helical shape between ends 177 and 178, but can be formed of a plurality of helical segments.

As with expandable supports 162 of FIGS. 9A and 9B, helical support member 172 can provide radial and circumferential stiffening to body 176 to allow for support against the pressures of anatomy and to form a body defining a tunnel for the insertion of instruments. Helical support member 172 can, however, allow for axial expansion and contraction of body 176 such that the native stiffness of body 176 can be utilized to allow for axial contraction and expansion of reinsertion sheath 170 to allow for deployment as is described with reference to FIGS. 9A and 9B.

Figures 11, 12A, 12B:
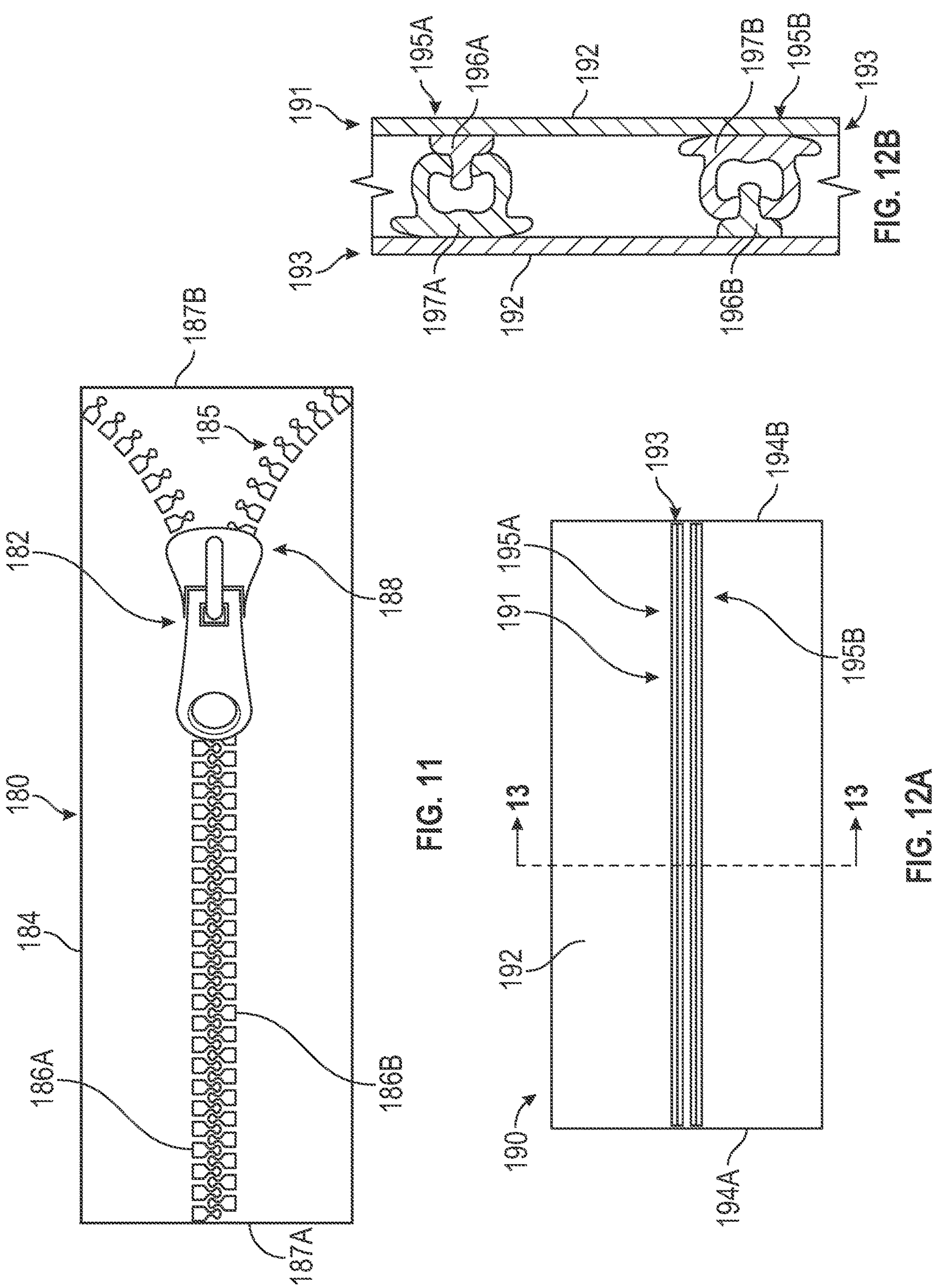
FIG. 11 is a schematic side view of a segment of a reinsertion sheath of the present disclosure having a zipper closure mechanism.
FIG. 12A is a schematic side view of a segment of a reinsertion sheath of the present disclosure having an interlocking rail closure mechanism.
FIG. 12B is a cross-sectional view taken along section 12B-12B of FIG. 12A showing rails of the interlocking rail closure mechanism.

FIG. 11 is a schematic side view of a segment of reinsertion sheath 180 of the present disclosure having zipper closure mechanism 182. Sheath 180 can comprise shaft 184 and slit 185. Shaft can extend from first side 187A to second side 187B. Zipper closure mechanism 182 can comprise opposing teeth 186A and 186B on opposite sides of slit 185 and shuttle 188. Zipper closure mechanism 182 is not necessarily drawn to scale in FIG. 11. Reinsertion sheath 180 of FIG. 11 can be used in conjunction with any reinsertion sheath described herein, such as reinsertion sheaths 104, 160 and 170. Zipper closure mechanism 182 can be configured to extend along any of slits 126, 169 and 179.

Teeth 186A can be positioned along one side of slit 185. Teeth 186B can be positioned along a second side of slit 185. Teeth 186A and 186B can be staggered so that teeth 186B can fit between teeth 186B and vice versa. Shuttle 188 can be used to couple and uncouple teeth 186A and 186B. As such, zipper closure mechanism 182 can function as a zipper in a conventional manner.

Zipper closure mechanism 182 can be released to allow teeth 186A and 186B to separate. As such, reinsertion sheath 180 can be positioned around a shaft of a scope. Reinsertion sheath 180 can be inserted into anatomy with first side 187A positioned distally to enter the anatomy first. As shaft 184 is pushed or fed distally into the anatomy, shuttle 188 can be pulled proximally to bring teeth 186A and 186B into engagement. Thus, as shaft 184 is unfurled and fed further into anatomy, shuttle 188 can be advanced to close-up shaft 184.

FIG. 12A is a schematic side view of a segment of reinsertion sheath 190 of the present disclosure having interlocking rail closure mechanism 191. Reinsertion sheath 190 can comprise shaft 192 and slit 193. Shaft 192 can extend from first end 194A to second end 194B. Interlocking rail closure mechanism 191 can comprise first rail 195A and second rail 195B. Interlocking rail closure mechanism 191 is not necessarily drawn to scale in FIG. 12A. Reinsertion sheath 190 of FIG. 12A can be used in conjunction with any reinsertion sheath described herein, such as reinsertion sheaths 104, 160 and 170 described herein. Interlocking rail closure mechanism 191 can be configured to extend along any of slits 126, 169 and 179.

First rail 195A and second rail 195B can be placed on ends of shaft 192 forming slit 193 in an overlapping manner, as is described with reference to FIG. 13.

FIG. 12B is a cross-sectional view of reinsertion sheath closure mechanism 191 of FIG. 12A. Interlocking rail closure mechanism 191 can comprise first rail 195A and second rail 195B. First rail 195A can comprise first projection 196A and first slot 197A. Second rail 195B can comprise second projection 196B and second slot 197B. Projections 196A and 196B can comprise bulbous heads and each rail of slots 197A and 197B can comprise inwardly oriented teeth configured to engage with the bulbous heads. In an example, interlocking rail closure mechanism 191 can be constructed according to U.S. Pat. No. 7,137,736 to Pawloski et al., which is hereby incorporated by reference in its entirety.

As shown in FIG. 12B, ends of slit 193 can be pulled so that portions of shaft 192 overlap to allow slots 197A and 197B and projections 196A and 196B to interface, respectively. Projection 196A and slot 197A can be placed in an overlapping arrangement and pressed together by an operator to lock. Likewise, projection 196B and slot 197B can be placed in an overlapping arrangement and pressed together by an operator to lock. In an example, a shuttle can be provided on interlocking rail closure mechanism 191 to facilitate pushing of projections 196A and 196B together with slots 197A and 197B and separation of said components. Either of ends 194A and 194B can be fed into anatomy first.

Figure 13:
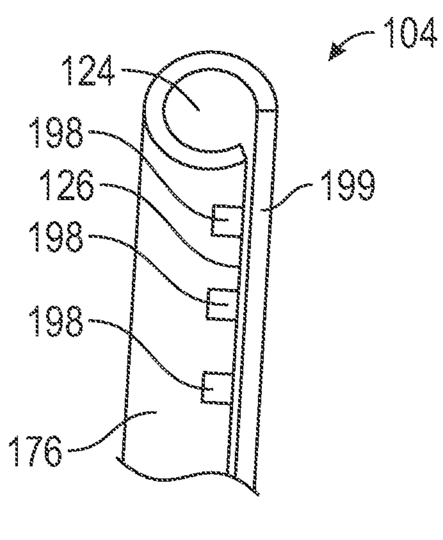
FIG. 13 is a schematic illustration of a reinsertion sheath comprising an elongate shaft comprising a lumen and a gap closeable by magnetic force.

FIG. 13 is a schematic illustration of reinsertion sheath 104 comprising elongate body 176 comprising lumen 124 and slit 126. Slit 126 can include a plurality of magnetic members 198 and metallic strip 199. Magnetic members 198 can be attracted to metallic strip 199 via magnetic forces. Thus, at rest, magnetic members 198 can pull ends of elongate body 176 along slit 126 closed. However, magnetic members 198 can be pushed away from metallic strip 199 to allow the device or object to enter lumen 124 in the radial direction. After the device or object enters lumen 124, magnetic members 198 can be pulled back into engagement with metallic strip 199 via magnetic attraction. As such, sheath 104 can be easily slipped over shaft 110 of scope 102 while scope 102 is inserted into anatomy.

FIGS. 6-13 illustrate examples of reinsertion sheaths of the present disclosure having various features that can be used together or separately or in various combinations thereof. Reinsertion sheaths of the present disclosure can provide a body that forms a tunnel through anatomy that can guide another instrument inserted therein to a desired location. The reinsertion sheaths can be positioned within anatomy using another instrument previously navigated (e.g., steered, turned, controlled and manipulated to be pushed through desired anatomical features and ducts) to a target tissue site in the anatomy. The previously inserted instrument can thus serve as a type of guide feature similar to a guide wire to direct reinsertion sheath to the target tissue site without having to actively navigate the reinsertion sheath or with minimal manipulation or cajoling. As discussed herein, the reinsertion sheaths can be circumferentially openable to allow positioning of the reinsertion sheath over an instrument in a radial direction relative to an axis of the instrument. Thus, the reinsertion sheaths can be positioned over a proximal end of the instrument while a distal end is positioned within anatomy. Material of the reinsertion sheaths can form skins radially reinforced with wires or bars and that can be axially compacted, e.g., contracted or furled, in an axial direction so as to fit over only a portion of the length of the instrument, e.g., a portion of the instrument not inserted into anatomy. As such, the reinsertion sheath can be more easily manipulated. Once positioned over the proximal portion of the inserted instrument, the reinsertion sheath can be expanded or unfurled to push a distal portion of the insertion sheath into anatomy of the patient around the instrument. Axially collapsible support features can be used to provide the reinsertion sheaths with radial rigidity to push anatomy away from the center axis of the reinsertion sheath. Thus, once the guide instrument is removed from the reinsertion sheath, an open tunnel can be provided within the reinsertion sheath to provide a direct route to the target tissue site.

Figure 14:
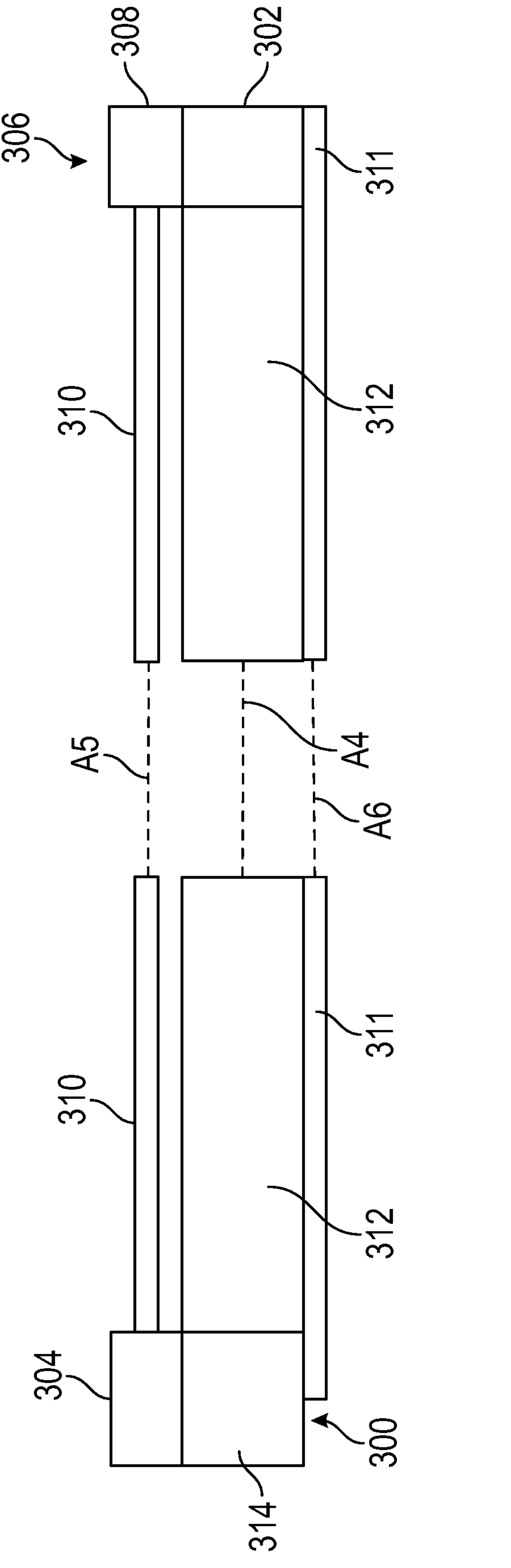
FIG. 14 is a schematic view of an endoscope comprising a suturing device connected to an electric motor via a drive system comprising a gear system and a shaft.

FIG. 14 is a schematic view of endoscope 300 comprising suturing device 302 connected to electric motor 304 via drive system 306 comprising gear system 308 and shaft 310. Endoscope 300 can further comprise tissue engaging device 311 that can be used to hold tissue for suturing device 302.

Figure 22:
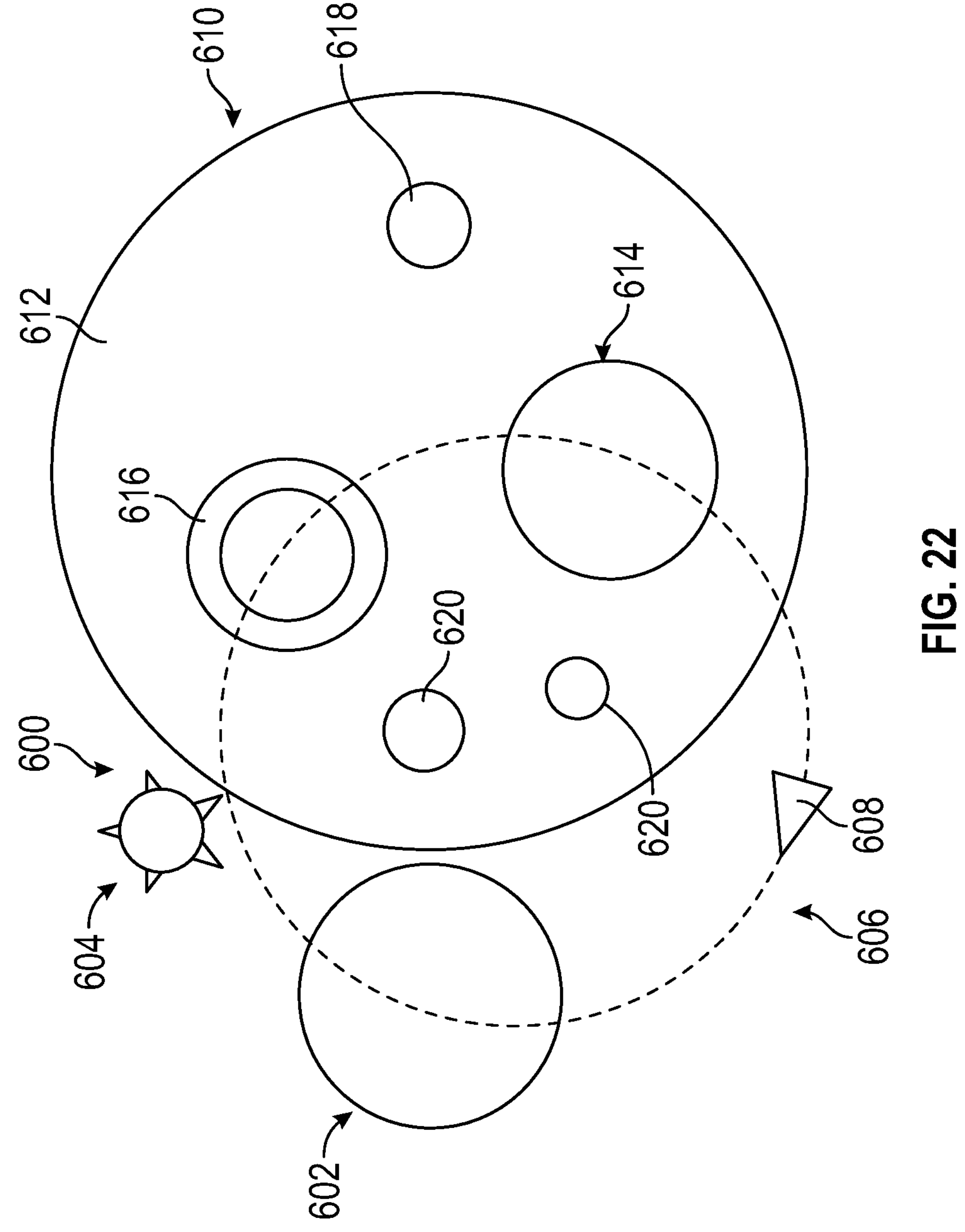
FIG. 22 is a schematic end view of a geared suturing device used in conjunction with an external working channel, wherein a pinion gear engages with outer gear teeth of a ring gear that directly drives a suturing element.
Figure 23:
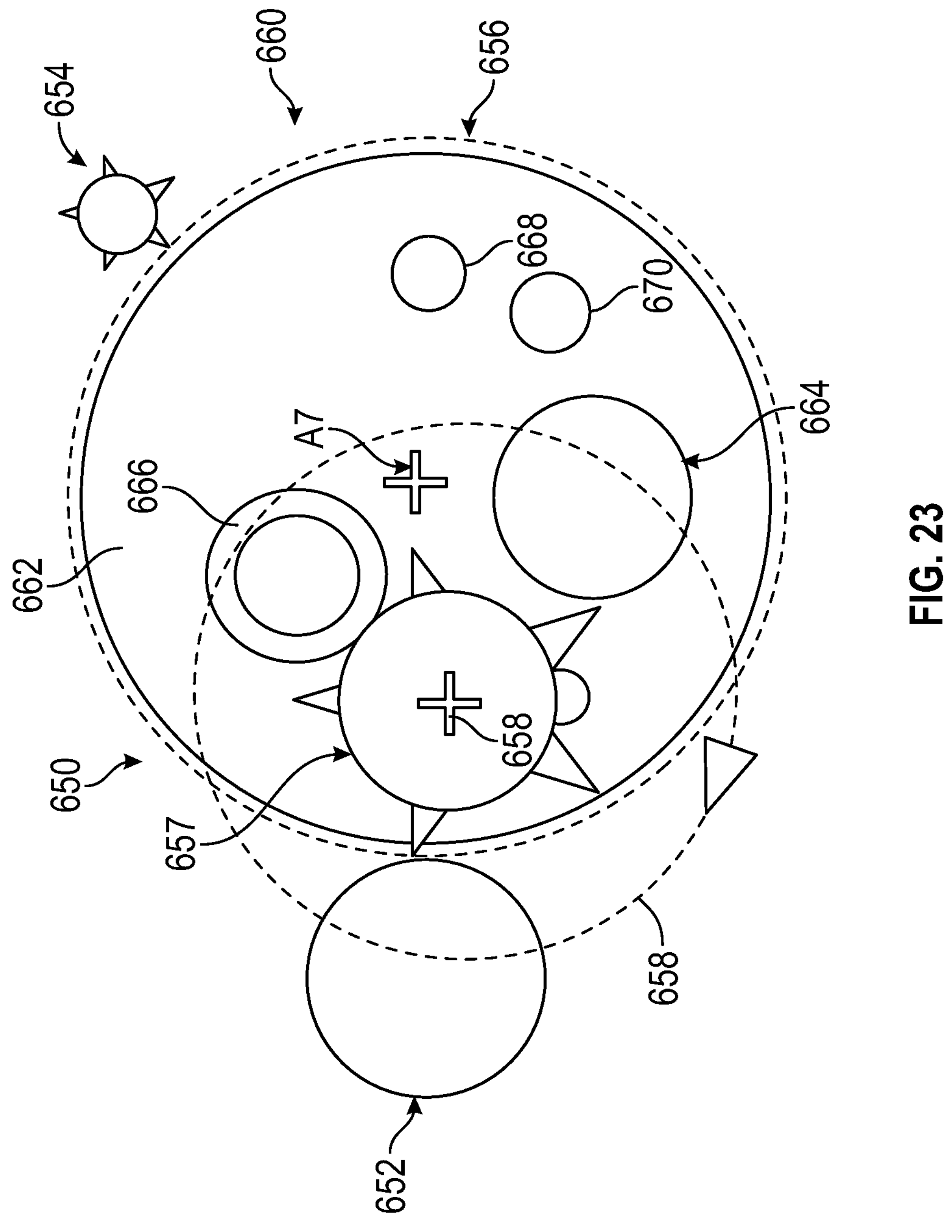
FIG. 23 is a schematic end view of the geared suturing device used in conjunction with an external working channel, wherein a pinion gear engages with outer gear teeth of a ring gear to indirectly drive a suturing element through an offsetting gear.

In examples, endoscope 300 can comprise a two-channel endoscope having internal channels for shaft 310 and tissue engaging device 311. As shown in FIGS. 22 and 23, either or both of shaft 310 and tissue engaging device 311 can be introduced through external working channels that run alongside endoscope 300. In examples, a separate external working channel is provided for a housing for a catch mechanism that facilitates pulling of suture material from a proximal location and the center of rotation for gear system 308 can be moved off-center of endoscope 300 to allow a suturing element to pick up a catch from the external working channel.

Endoscopes 300 can be constructed according to any of the scopes described herein. Endoscope 300 can comprise shaft 312 and controller 314. Controller 314 can be configured to operate features of endoscope 300, as well as motor 304, suturing device 302 and tissue engaging device 311. Shaft 312 of endoscope 300, which is shown broken away in FIG. 14, can extend along axis A4.

Motor 304 can be coupled to endoscope 300, such as at controller 314. Motor 304 can comprise an electric motor configured to receive electrical power from controller 314 or an external source. In examples, motor 304 can comprise a miniature electric motor. In additional examples, motor 304 can comprise or can be replaced with a manual input, such as a crank handle or knob to allow a user of endoscope 500 to impart rotation in shaft 310 with a mechanical advantage. For example, shaft 310 can be mechanically actuated utilizing a push/pull mechanism with a corkscrew style rotation path. Gear system 308 can be connected to suturing device 302. Gear system 308 can comprise a part of suturing device 302 or can be a separate, couplable component. Shaft 310, which is shown broken away in FIG. 14, can extend along shaft 312 of endoscope 300 along axis A5. In the illustrated example, shaft 310 can be attached to the exterior of shaft 312. In other examples, shaft 310 can extend through shaft 312. In either configuration, axis A5 can be parallel to axis A4. However, in other examples, shaft 310 can be non-parallel with shaft 312.

Suturing device 302 can comprise a device for implanting or applying suture material to tissue. For example, suturing device 302 can comprise a device for advancing a suturing element, such as a needle, to extend one or more strands of suturing material through tissue, such as by pulling suturing material behind. Suturing device 302 can utilize rotational output of motor 304, as transmitted through shaft 310 and gear system 308, to advance the suturing element. Gear system 308 can convert rotational output of shaft 310 to a useable input for suturing device 302. In examples, gear system 308 can comprise a spur gear system, a herringbone gear system, a bevel gear system, a worm gear system, a rack and pinion gear system or an internal gear system. In examples, gear system 308 can comprise the gear systems of FIGS. 22 and 23 that can allow for off-axis suturing. Gear system 308 can be used to produce a circulating or reciprocating motion of a suturing element to push or pull suturing material through tissue. For example, the suturing element can be driven in a circumferential direction about axis A4 or along another axis parallel to axis A4. In examples, the suturing element can be reciprocated in similar circumferential directions. In other examples, the suturing element can be reciprocated along axis A4 or another axis parallel to axis A4. Reciprocating motion can be produced by reversing the rotational direction of shaft 310 or via use of a mechanism that can convert uni-directional rotational input into bi-directional output, such as crankshaft and orbital couplings.

Tissue engaging device 311 can comprise a device that can pull tissue close to suturing device 302 and hold the tissue in place to allow the suturing element to place through the tissue in a precise location. Tissue engaging device 311 of endoscope 300, which is shown broken away in FIG. 14, can extend along axis A6. In examples, tissue engaging device 311 can comprise a tube to allow another device, such as forceps, to pass therethrough. In examples, tissue engaging device 311 can comprise a suction tube through which a vacuum can be drawn to pull tissue toward suturing device 302. Tissue engaging device 311 can allow for insertion of an instrument or suction tube or for coupling to a suction source through controller 314 or via direct insertion or coupling.

In examples, suturing device 302 and tissue engaging device 311 can comprise one or more attachments that can be coupled to conventional endoscopes. Additionally, suturing device 302 and tissue engaging device 311 can be incorporated into an endoscope so as to not be user-removable. In various examples, suturing device 302 can be used with an endoscope to eliminate the need for having to use an additional dedicated suturing device. Likewise, suturing device 302 can be used without tissue engaging device 311 when, for example, endoscope 300 includes working channels that can accept forceps or suction tubes.

Figure 15:
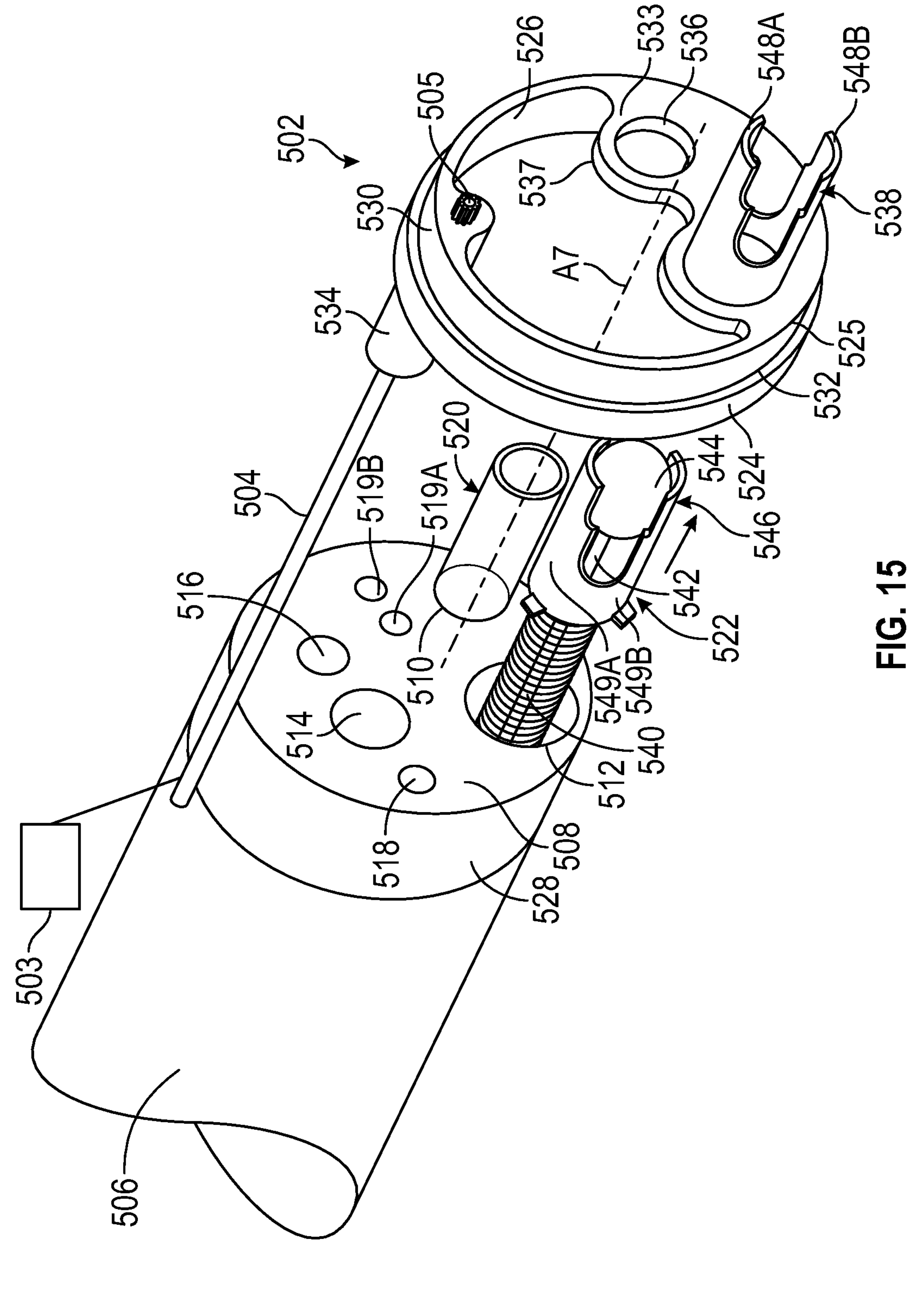
FIG. 15 is an exploded view of a distal end of an endoscope and a geared suturing device having a drive shaft and a pinion gear.

FIG. 15 is an exploded view of endoscope 500 and geared suturing device 502 having drive shaft 504 and pinion gear 505. Drive shaft 504 can be connected to motor 503. Endoscope 500 can be constructed according to any of the scopes described herein. As discussed herein, suturing device 502 can comprise a device for driving a suturing element, such as a needle, staple, shuttle and the like, to pull and/or push suturing material through tissue. In examples, electric motor 503 can be used to move an arcuate or helical suturing needle via a geared connection. Although suturing device 502 is described as being a separately attachable device to endoscope 500, in additional examples, suturing device 502 or components thereof (e.g., mounting ring 524, drive shaft 504 and socket 538) can be integrated directly into endoscope 500.

Endoscope 500 can comprise shaft 506 having end face 508, which can include working channel 510 and suturing channel 512, as well as various other components including imaging lens 514, illumination lens 516, irrigation channel 518, auxiliary channels 519A and 519B and other components typically used on endoscopes. Instrument 520 can be positioned in working channel 510 or auxiliary channels 519A and 519B to perform a medical intervention. In the illustrated example, auxiliary instrument 520 can comprise a vacuum tube, but can comprise a forceps in other examples. Suture tube 522 can comprise a device for providing suturing material to suturing device 502.

Suturing device 502 can comprise mounting ring 524 to which pinion gear 505 can be mounted. Mounting ring 524 can comprise a main housing to which other components of suturing device 502 can be mounted. Mounting ring 524 can include axial extension 525 that projects forward of end face 508. Axial extension 525 can include seat 530 that extend around an outer diameter surface. Seat 530 can comprise a surface upon which retaining ring 570 (FIG. 17) mounts. In examples, seat 530 can be recessed radially inward of the outer diameter surface of mounting ring 524 so that shoulder 532 can be formed. Mounting ring 524 can comprise socket 534 for receiving drive shaft 504. Socket 534 can hold pinion gear 505 axially distal of seat 530. Mounting ring 524 can additionally comprise end plate 533, outlet 536, opening 537, and socket 538. Opening 537 can provide features of end face 508 of endoscope 500 access through mounting ring 524. Outlet 536 can allow working channel 510 access to the distal side of mounting ring 524. Socket 538 can comprise a receptacle for receiving suture tube 522. End plate 533 can hold outlet 536 and socket 538 in a fixed relationship. Socket 538 can be mounted on end plate 533 to extend distally of mounting ring 524 so as to be positioned distally and in view of imaging lens 514 and illumination lens 516.

Mounting ring 524 can comprise a rigid or compliant body that facilitates coupling with shaft 506. Mounting ring 524 can be sized to fit around end face 508 of endoscope 500. Mounting ring 524 can comprise an annular body having side wall 526 passing through from one end to the other end along axis A7. Shaft 506 can extend along axis A7. Shaft 506 of endoscope 500 can be sized to fit into side wall 526 in a concentric manner to retain suturing device 502 attached to endoscope 500. Mounting ring 524 can be coupled to shaft 506 via interference fit, threaded coupling or other suitable means. For example, side wall 526 of ring 524 can be threadedly engaged with outer surface 528 of shaft 506. In examples, an interference fit can be formed between side wall 526 and shaft 506. Side wall 526 can extend straight to the proximal end of mounting ring 524 and can include end plate 533 to prevent mounting ring 524 from being pushed proximally along shaft 506. Such an end plate can ensure proper positioning of outlet 536 and socket 538 relative to end face 508 to ensure suture tube 522 is within the field of view of imaging lens 514 and illumination lens 516. However, side wall 526 can allow enough of end face 508 to be exposed to not interfere with working channel 510, suturing channel 512, imaging lens 514, illumination lens 516 and irrigation channel 518. Mounting ring 524 can, therefore, form a cap that can be releasably attached to shaft 506. Side wall 526 and shaft 506 can additionally include features (not visible in FIG. 15) to facilitate rotational alignment between suturing device 502 and endoscope 500, such as to provide proper orientation between working channel 510, irrigation channel 512, imaging lens 514, illumination lens 516 and irrigation channel 518 of endoscope 500 and side wall 526 of mounting ring 524. In examples, the rotational alignment features can comprise an axially extending channel extending into end face 508 at a particular circumferential location that can receive a corresponding axially extending flange on side wall 526, or the reverse configuration. In examples, side wall 526 of mounting ring 524 can have locating features like a flat side that mates with a corresponding flat side on shaft 506 to, for example, align suturing channel 512 of endoscope 500 with socket 538 of mounting ring 524.

Suture tube 522 can comprise tube 540, in which is positioned suture strand 542, stop 544 and holder 546. Tube 540 can comprise an elongate body having an internal lumen that extends from distal end face 508 to the proximal end of endoscope 500. Tube 540 can allow for a supply of suture material to be connected to end face 508. Thus, the proximal end of suture strand 542 can be wound around a spool in order for a supply of suturing material to be provided to suturing device 502. The distal end of suture strand 542 can be connected to stop, or anchor, 544. Stop 544 can comprise a ball or another shaped body, that provides a mechanism for engaging with suturing device 502 and that can anchor, e.g., prevent passing through punctures in tissue, suture strand 542. Stop 544 can be attached to suture strand 542 via any suitable mechanism, such as by being threaded through a bore in stop 544 and being tied off or stop 544 can be crimped onto suture strand 542. Holder 546 can comprise a body for holding stop 544 to allow for engagement with suturing device 502, which can be configured to pull suture strand 542 from tube 540.

Holder 546 can be shaped similarly to socket 538 and holder 546 can be sized to fit within socket 538. Holder 546 and socket 538 can be configured to hold stop 544 in a specific location relative to mounting ring 524 to allow suturing device 502 to engage with stop 544 and suture strand 542. Holder 546 and socket 538 can provide an open passage in the axial direction to allow suturing material to extend therethrough. Holder 546 and socket 538 can comprise radial openings to allow for suturing device 502 to pass radially through holder 546 and socket 538. For example, socket 538 can comprise upper portion 548A and lower portion 548B. Likewise, holder 546 can comprise upper portion 549A and lower portion 549B. Socket 538 and holder 546 can allow stop 544 to be firmly seated within suturing device 502, but that also allows the suturing element, e.g., needle 552 of FIG. 16, to push and/or pull stop 544 from socket 538 and holder 546. In examples, upper portion 548A and lower portion 548B can be deflectable in a radial outward direction to facilitate insertion and removal of stop 544.

Figure 16:
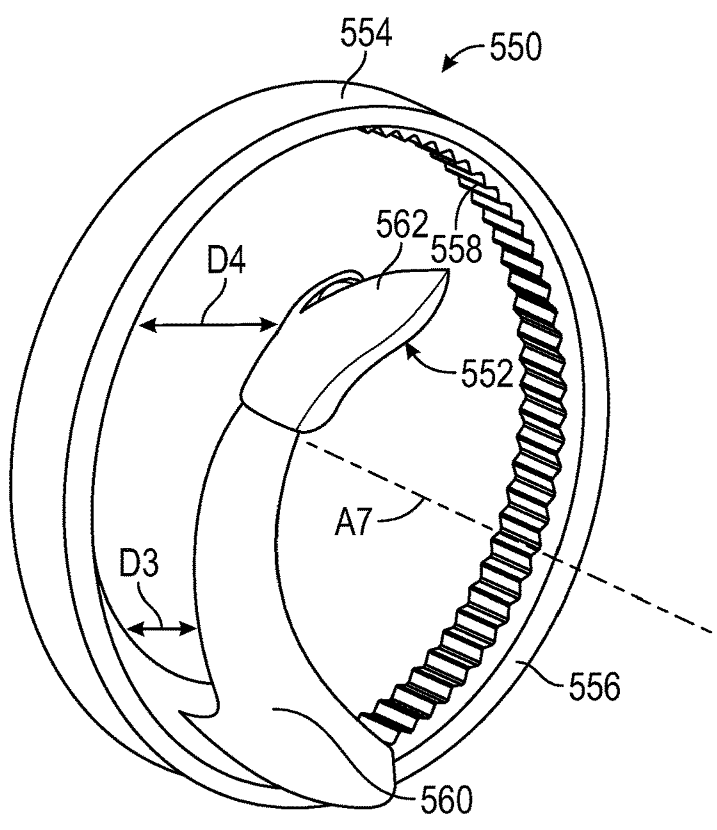
FIG. 16 is a perspective view of ring gear having a rotating needle for coupling with the pinion gear of FIG. 15.

FIG. 16 is a perspective view of ring gear 550 having rotating needle 552 for coupling with pinion gear 505 of FIG. 15. Ring gear 550 can comprise a component of suturing device 502. Ring gear 550 can comprise ring body 554, flange 556, gear teeth 558 and needle 552. Needle 552 can comprise needle body 560 and needle tip 562. Gear teeth 558 can be configured to engage with pinion gear 505. Ring gear 550 can be configured to be positioned axially distal of mounting ring 524 so that radially outward pointing gear teeth of pinion gear 505 engage with gear teeth 558 and flange 556 engages with the distal tip of pinion gear 505. As such, pinion gear 505 can drive ring gear 550 to rotate about axis A7. As discussed with reference to FIG. 17, retaining ring 570 can be used to support ring gear 550. Ring gear 550 can be made of a rigid material, such as stainless steel, to allow for firm engagement of gear teeth 558.

Needle body 560 can comprise a curved body having a first end coupled to ring body 554 and a second end attached to needle tip 562. In examples, needle body 560 can comprise an arcuate segment having a smaller radius of curvature than ring body 554. In examples, needle body 560 can comprise a curved body extending along a non-circular path. Needle body 560 can be configured to position needle tip 562 for engagement with socket 538. In examples needle body 560 can extend along a helical or corkscrew path such that in addition to being circumferentially curved about axis A7, distance D4 can be greater than distance D3 such that needle body 560 extends axially along axis A7. Needle body 560 can be made of a rigid material, such as stainless steel, to allow needle tip 562 to be driven through tissue. Needle body 560 can be integral with ring body 554.

Figure 17:
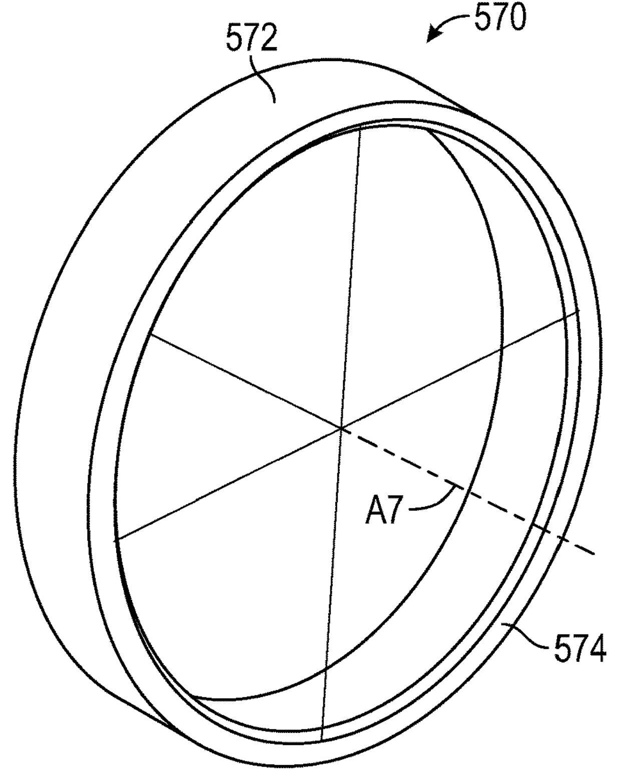
FIG. 17 is a perspective view of a retaining ring configured to hold the ring gear of FIG. 16 in engagement with the electric suturing device of FIG. 15.

FIG. 17 is a perspective view of retaining ring 570 configured to hold ring gear 550 of FIG. 16 in engagement with mounting ring 524 of FIG. 15. Retaining ring 570 can comprise a component of suturing device 502. Retaining ring 570 can comprise ring body 572 and flange 574. Ring body 572 of retaining ring 570 can fit over ring body 554 of ring gear 550 and extend onto mounting ring 524. Flange 574 can extend radially inward and can abut flange 556 to trap ring gear 550 between mounting ring 524. Ring body 572 can fit onto mounting ring 524 via interference fit and can allow ring gear 550 to rotate freely between mounting ring 524 and retaining ring 570. Retaining ring 570 can be made of rigid material, such as stainless steel, or a resilient material, such as plastic or rubber.

Figure 18:
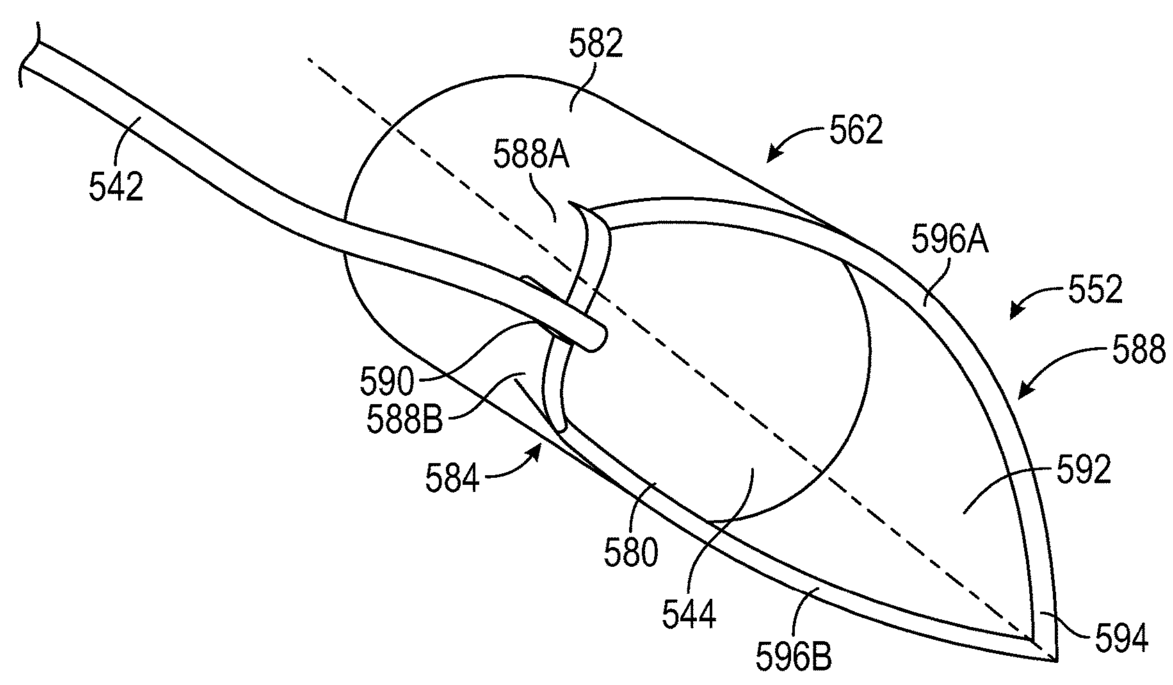
FIG. 18 is a perspective view of a tip of the rotating needle of FIG. 16 showing a socket for holding a suturing anchor.
Figure 19:
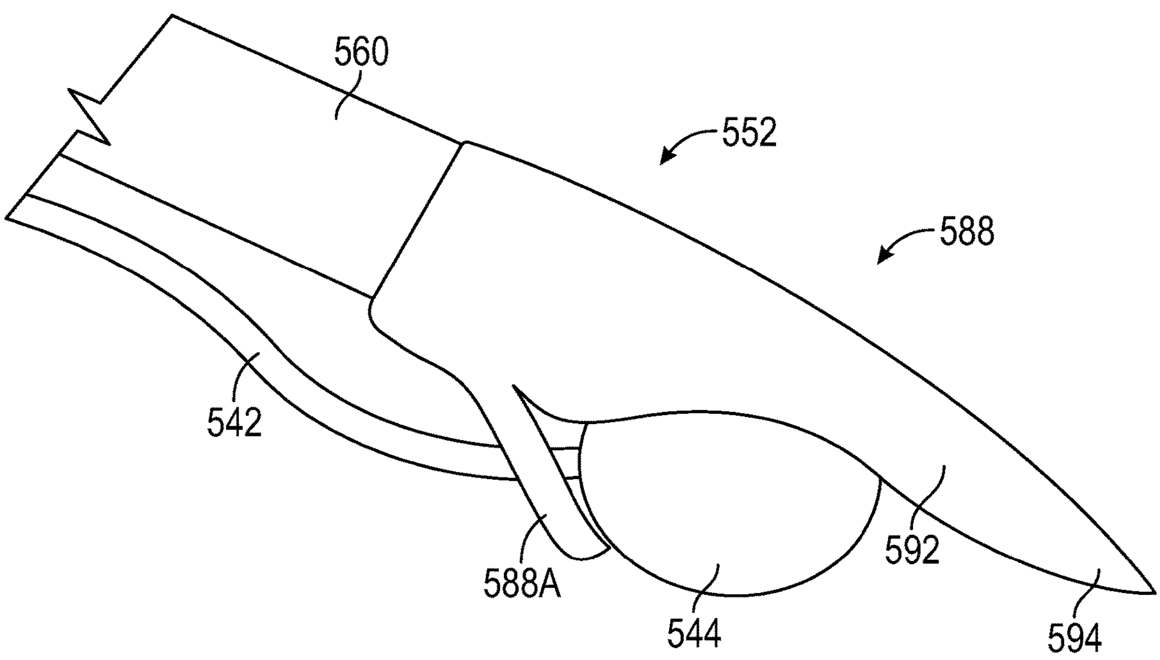
FIG. 19 is a perspective view of the tip of the rotating needle of FIG. 18 showing a suturing anchor held in the socket.

FIG. 18 is a perspective view of tip 562 of rotating needle 552 of FIG. 16 showing socket 580 for holding stop 544. FIG. 19 is a perspective view of tip 562 of rotating needle 552 of FIG. 18 showing stop 544 held in socket 580. FIGS. 18 and 19 are discussed concurrently.

Socket 580 can comprise cylindrical body 582, suture guide 584, and blade 586. Cylindrical body 582 can comprise a component for attaching to needle body 560. Cylindrical body 582 can comprise a partial or complete ring, or another shaped body, to couple to needle body 560. In examples, cylindrical body 582 can be attach to needle body 560 via an interference fit. Suture guide 584 can comprise a component or device to receive suture strand 542. Suture guide 584 can comprise first arm 588A, second arm 588B and notch 590. Suture guide 584 can be configured to allow stop 544 to be seated within socket 580 without interference from suture strand 542. Blade 586 can comprise a body configured to pierce tissue. Blade 542 can comprise curved wall 592 and point 594. Curved wall 592 can be configured to simultaneously hold stop 544 in opposition to suture guide 584 and position point 594 distally of stop 544. Edges 596A and 596B of curved wall 592 can slope from point 594 to suture guide 584. Edges 596A and 596B can be sharpened to facilitate slicing through tissue.

Configured as such, socket 580 can be configured to hold stop 544 while needle 552 is rotated. For example, socket 580 can be shaped to cup or hold stop 544 when needle 552 is driven toward stop 544, clockwise with reference to FIG. 16, but can allow stop 544 to be removed from socket 580 when needle 552 is driven away from stop 544, counter-clockwise with reference to FIG. 16. In examples, tension on suture strand 542 can facilitate retention of stop 544 within socket 580.

Figure 20:
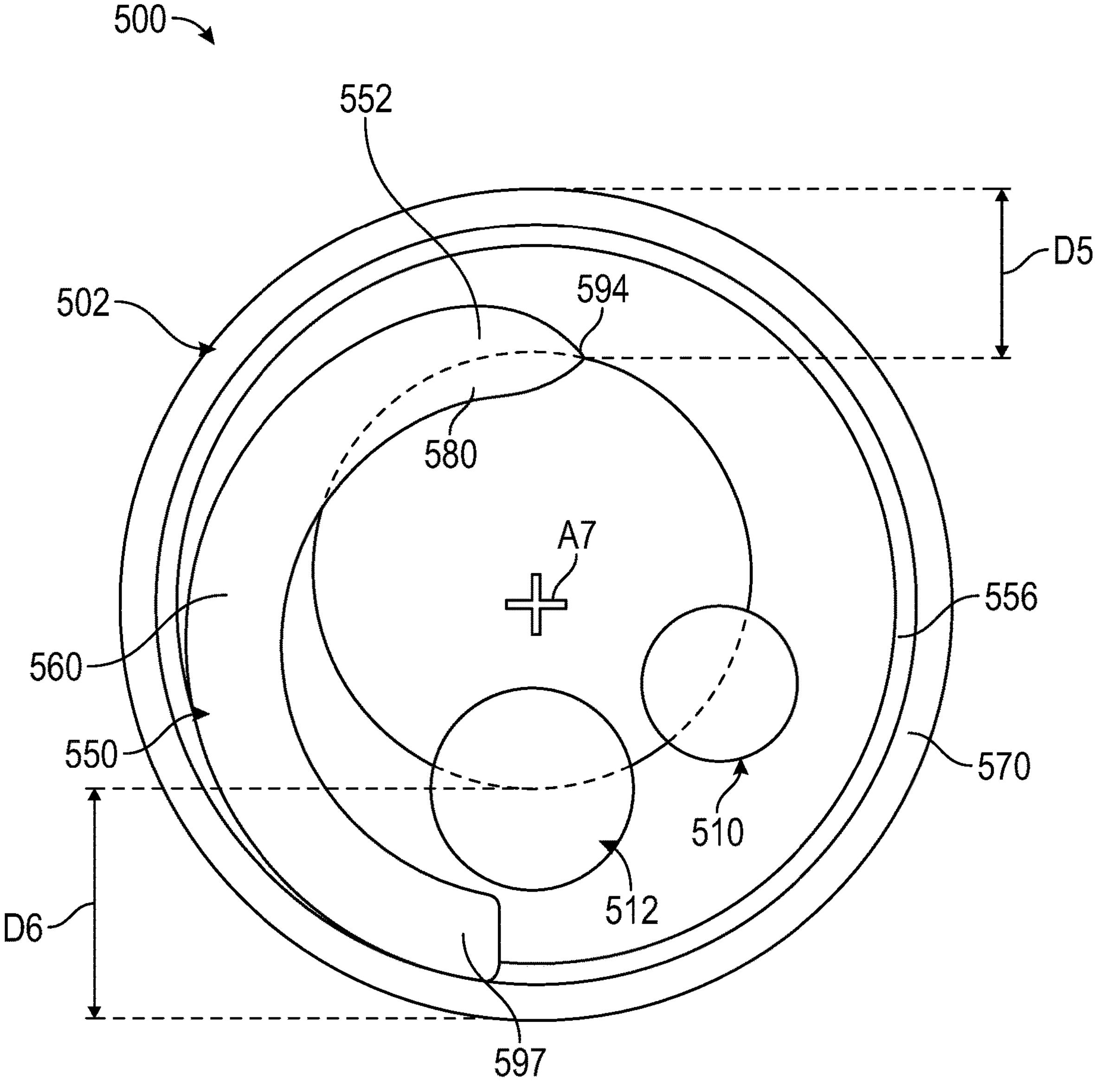
FIG. 20 is a schematic end view of the endoscope of FIG. 15 showing the suturing device relative to working channels of a shaft of the endoscope.

FIG. 20 is a schematic end view of endoscope 500 of FIG. 15 showing suturing device 502 relative to working channel 510 and suturing channel 512 of shaft 506 of endoscope 500. Needle 552 can be configured to rotate about axis A7 of shaft 506. Needle body 560 can be curved and can curl toward axis A7. Base 597 of needle body 560 can be connected to ring gear 550 at the outer diameter of ring body 554 (FIG. 16), while point 594 can be located inward of ring body 554 to provide needle body 560 with a radius of curvature that is smaller than ring body 554. Point 594 of needle 552 can be located distance D5 from axis A7. The center of suturing channel 512 can be located distance D6 from axis A7. Distance D5 can be approximately equal to distance D6 such that rotation of needle 552 can cause socket 580 to engage stop 544 emanating from suturing channel 512, such as via suture tube 522 (FIG. 15).

Various principles of operation of rotary-driven suturing devices of the present disclosure, particularly suturing device 502 of FIGS. 15-20, are described as follows with reference to FIGS. 21A-21F.

Figure 21A:
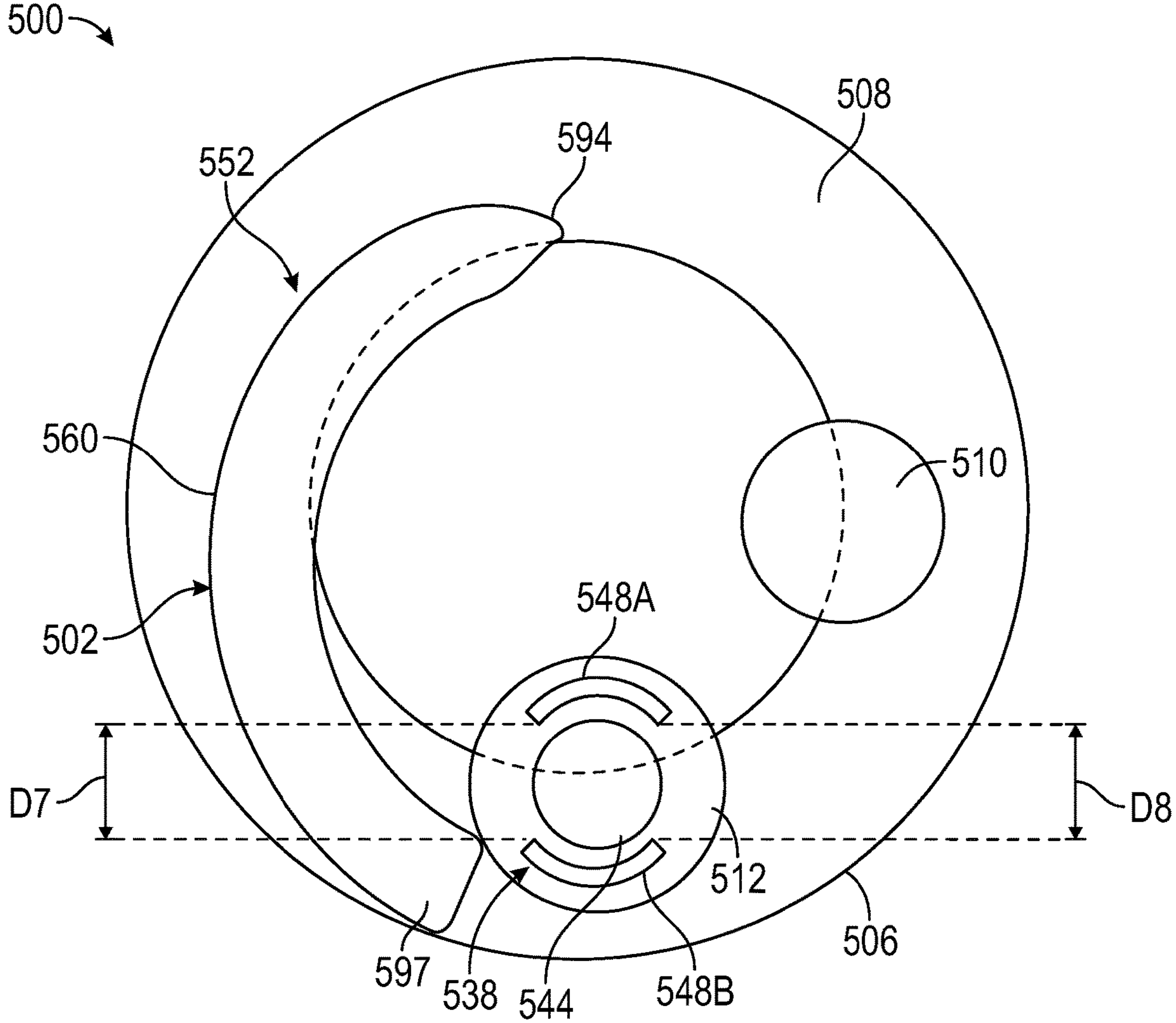
FIG. 21A is a schematic view of the suturing device of the present disclosure showing the suturing needle in a home position relative to a suture material channel and a suction channel.

FIG. 21A is a schematic view of suturing device 502 of the present disclosure showing suturing needle 552 in a home position relative to suturing channel 512 and working channel 510. FIG. 21A can correspond to a first step or operation of a method for implanting suture material into tissue using a geared suturing mechanism. In the home position of FIG. 21A, suturing needle 552 can be located so that point 594 is positioned away from suturing channel 512. Suturing needle 552 can be positioned to not block or interfere with suturing channel 512 and working channel 510. In the illustrated example, point 594 is positioned above suturing channel 512 approximately one-hundred-eighty degrees away from suturing channel 512. Thus, for discussion purposes, point 594 can be considered to be at the 12 o'clock position and stop 544 can be held in the 6 o'clock position by socket 538.

Stop 544 can be held within socket 538 between upper portion 548A and lower portion 548B. Socket 538 can hold stop 544 in the path of point 594. Socket 538 can be configured to allow needle body 560 to pass between upper portion 548A and lower portion 548B. For example, the left side of upper portion 548A can be spaced distance D7 from the left side of lower portion 548B and the right side of upper portion 548A can be spaced distance D7 from the right side of lower portion 548B, thereby allowing point 594 to pass between upper portion 548A and lower portion 548B due, in part, to point 594 being axially spaced from base 597 of needle body 560. In examples, distances D7 and D8 can be equal. However, in other examples, distances D7 and D8 can be different to facilitate stop 544 being inserted and removed from socket 538 in only one direction. In the illustrated example, distance D7 can be greater than distance D8. As such, point 594 can enter the right side of socket 538 in a clock-wise motion without stop 544 to remove stop 544 from socket 538 on the left side of socket 538 or can enter the right side of socket 538 in a clock-wise motion with stop 544, via deflection of portions 548A and 548B, to place stop 544 in socket 538. Also, in such configuration, point 594 can enter socket 538 from the left with stop 544 to place stop 544 in socket 538 due to portions 548A and 548B grabbing stop 544 from point 594.

Figure 21B:
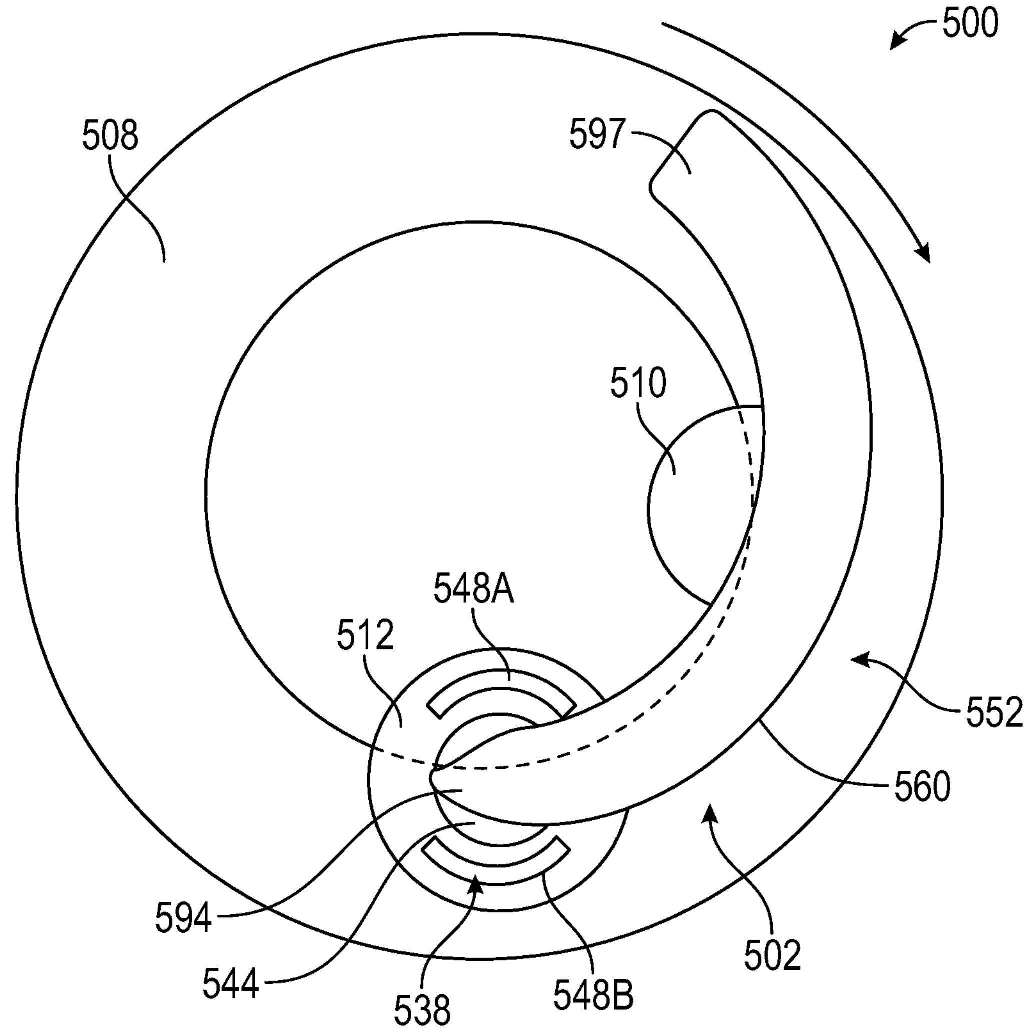
FIG. 21B is a schematic view of the suturing needle rotated clockwise to receive the anchor from the suturing channel.

FIG. 21B is a schematic view of suturing needle 552 rotated clockwise to receive stop 544 from suturing channel 512. FIG. 21B shows suturing needle 552 in a pick-up position. FIG. 21B can correspond to a second step or operation of a method for implanting suture material into tissue using a geared suturing mechanism. In the pick-up position of FIG. 21B, suturing needle 552 can be located so that point 594 is positioned at suturing channel 512. Suturing needle 552 can extend across working channel 510. In the illustrated example, point 594 is positioned at suturing channel 512. Thus, for discussion purposes, point 594 can be considered to be at the 6 o'clock position, where socket 580 can pick up stop 544. Needle body 560 can be rotated by motor 503 in the clock-wise direction to move point 594 into socket 538. Socket 580 (FIG. 18) of needle 552 can receive stop 544 from socket 538. Suturing needle 552 can continue to rotate and stop near the 11-12 o'clock position, as shown in FIG. 21C.

Figure 21C:
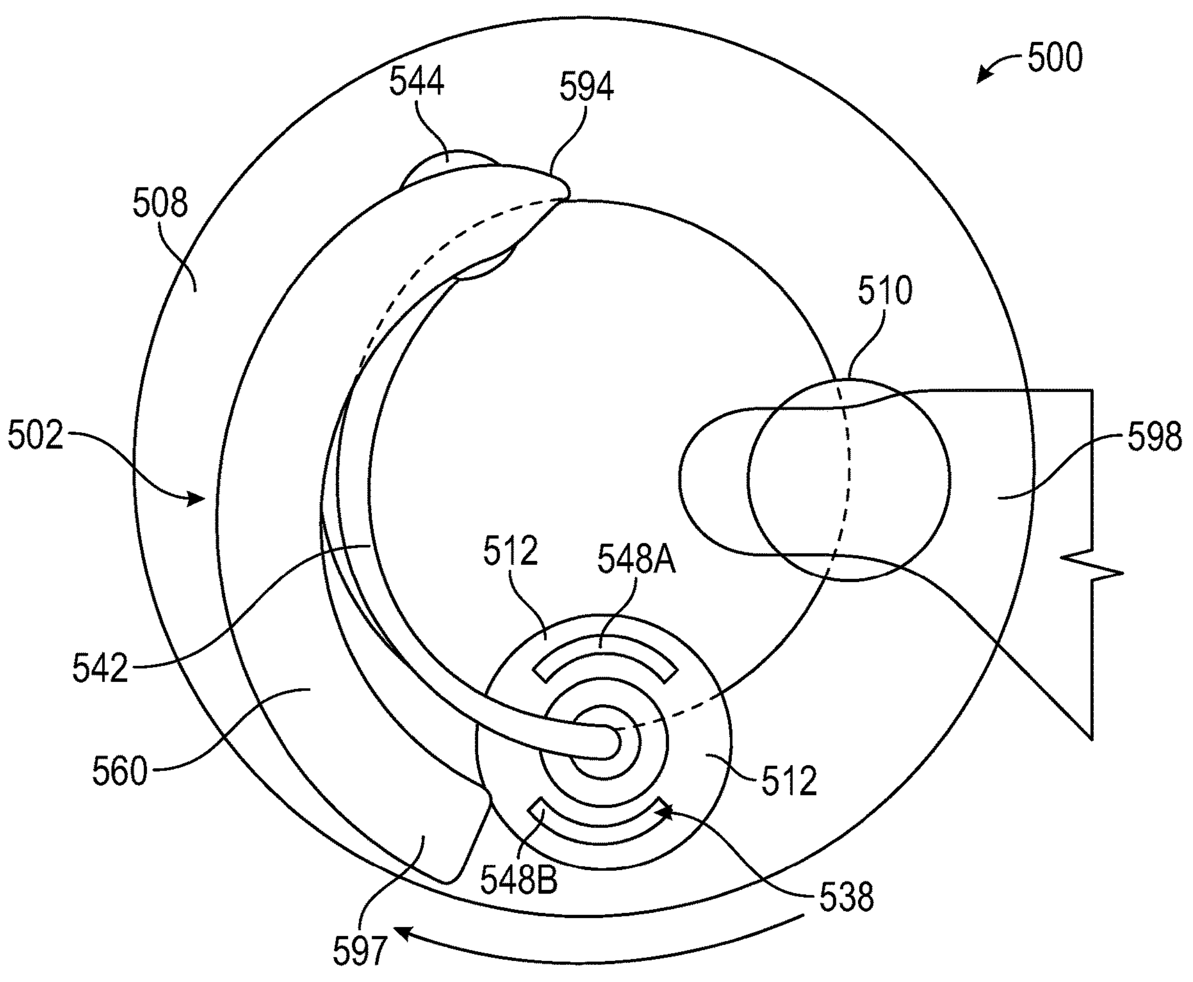
FIG. 21C is a schematic view of the suturing needle rotated clockwise to pull suturing material toward tissue held by the suction channel.

FIG. 21C is a schematic view of suturing needle 552 rotated clockwise to pull suture strand 542 toward tissue 598 held by suction channel 510. FIG. 21C shows suturing needle 552 in a standby position. FIG. 21C can correspond to a third step or operation of a method for implanting suture material into tissue using a geared suturing mechanism. In the standby position of FIG. 21C, suturing needle 552 can be armed with stop 544 and can be located so that point 594 and stop 544 can be located away from suturing channel 512 and working channel 510. Thus, for discussion purposes, point 594 and stop 544 can be considered to be at the 12 o'clock position. Needle body 560 can be rotated by motor 503 in the clock-wise direction to move point 594 out of socket 538. Socket 580 (FIG. 18) of needle 552 can release stop 544 from socket 538. Stop 544 can pull along suture strand 542, which can be positioned to align with suture guide 584 (FIG. 18).

Working channel 510 can be used to facilitate interaction with tissue 598. For example, a forceps can be extended from working channel 510 to grasp tissue 598. In additional examples, suction can be applied from working channel 510, either directly from working channel 510 or via a suction tube extended into working channel 510. The forceps or suction force can be used to pick-up or pull tissue 598 close to endoscope 500. In particular, the forceps or suction force can hold tissue 598 within the path of suturing needle 552. The forceps or suction force can hold tissue 598 in the 3 o'clock position.

Figure 21D:
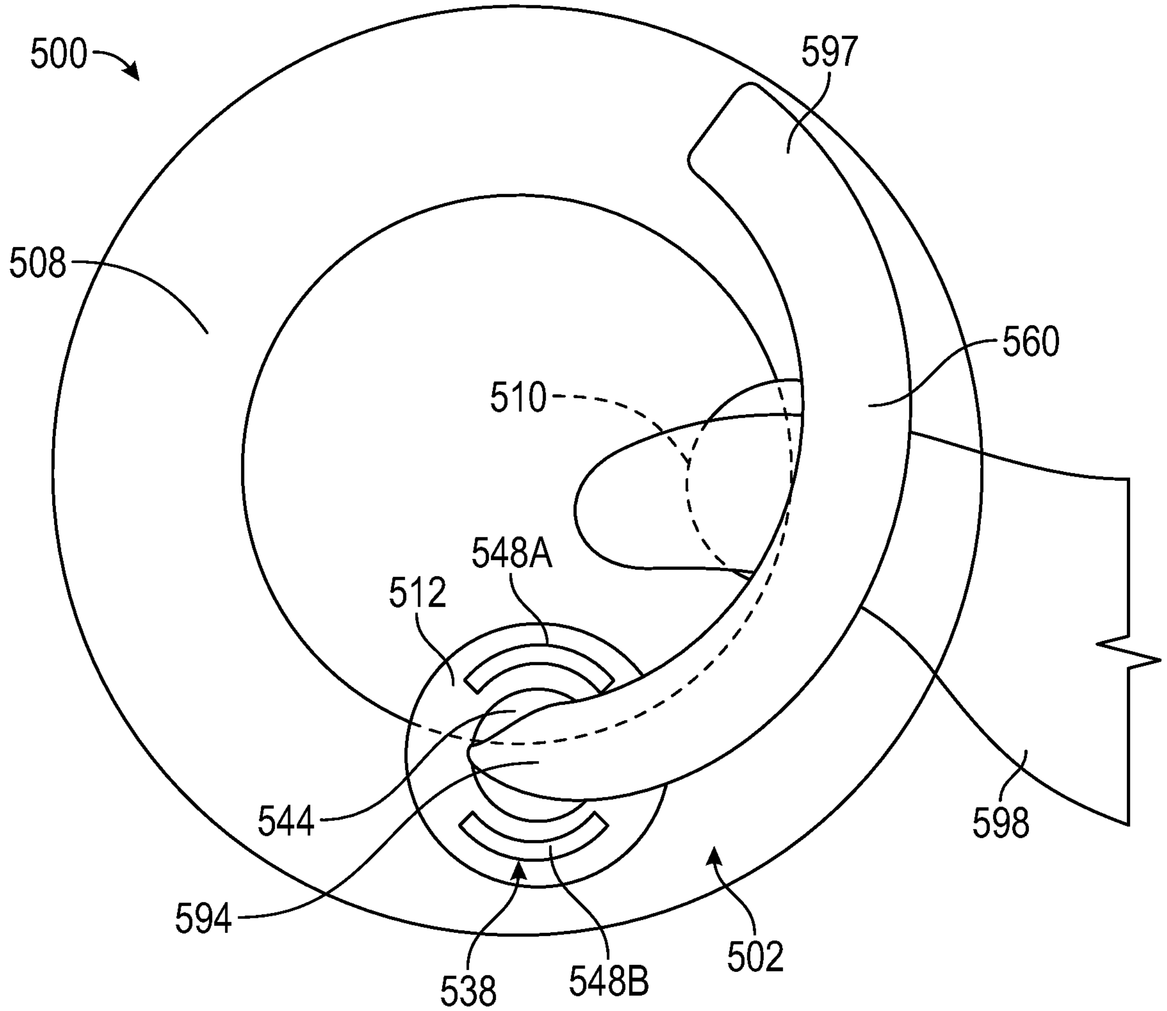
FIG. 21D is a schematic view of the suturing needle rotated clockwise to push the anchor and suturing needle through the tissue and push the anchor back to the suturing channel.

FIG. 21D is a schematic view of suturing needle 552 rotated clockwise to push stop 544 and point 594 through tissue 598 and push stop 544 to suturing channel 512. FIG. 21D shows suturing needle 552 in a suture position. FIG. 21D can correspond to a fourth step or operation of a method for implanting suture material into tissue using a geared suturing mechanism. In the suture position of FIG. 21D, needle body 560 can be rotated by motor 503 in the clock-wise direction to move point 594 and stop 544 through tissue 598. In the illustrated example, suturing needle 552 can be advanced through tissue 598 such that point 594 and stop 544 are back at suturing channel 512 and, for discussion purposes, point 594 and stop 544 can be considered to be at the 6 o'clock position.

Figure 21E:
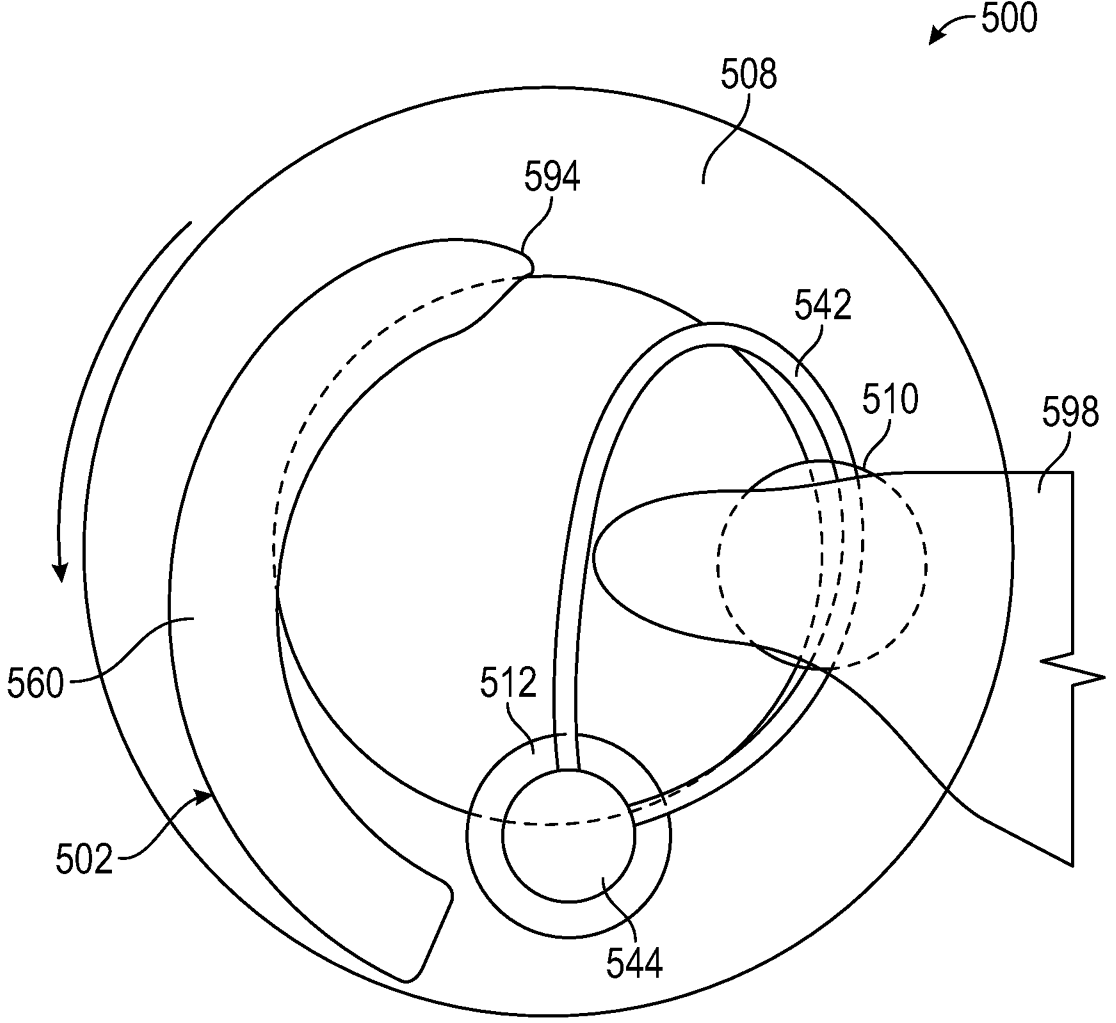
FIG. 21E is a schematic view of the suturing needle rotated counterclockwise leaving the anchor back at the suturing channel.

FIG. 21E is a schematic view of the suturing needle rotated counterclockwise leaving the anchor back at the suturing channel. FIG. 21E shows suturing needle 552 in the home position. FIG. 21E can correspond to a fifth step or operation of a method for implanting suture material into tissue using a geared suturing mechanism. FIG. 21E shows needle 552 being positioned back at the home position with one loop of suture strand 542 extending through tissue 598. From the position of FIG. 21D, needle 552 can be rotated counter-clockwise to leave stop 544 in socket 538 with suture strand 542 extending therefrom. In the home position, needle 552 is again ready to perform another cycle of suturing operations in tissue 598.

Figure 21F:
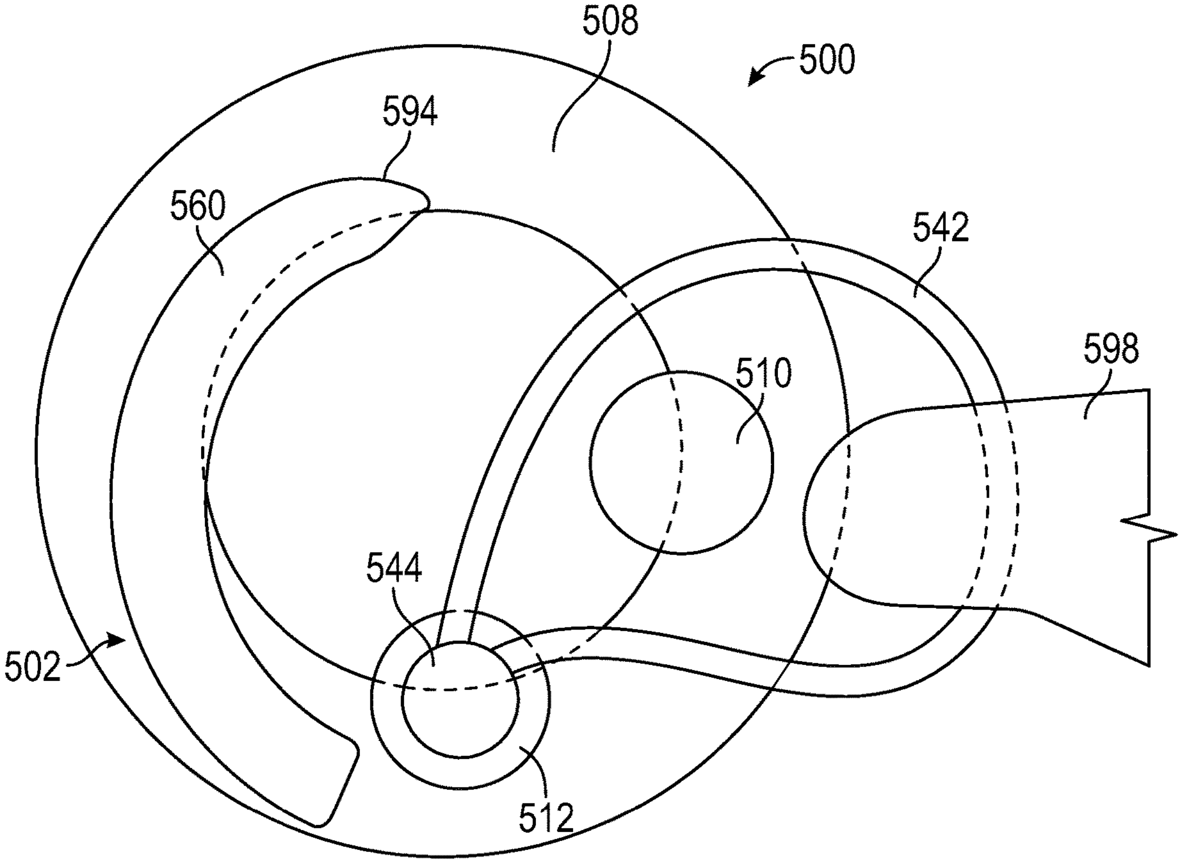
FIG. 21F is a schematic view of the suturing needle returned to the home position and a strand of suture material through the tissue.

FIG. 21F is a schematic view of the suturing needle returned to the home position and a strand of suture material through the tissue. FIG. 21F shows suturing needle 552 in the home position. FIG. 21F can correspond to a sixth step or operation of a method for implanting suture material into tissue using a geared suturing mechanism. FIG. 21F shows needle 552 positioned to repeat steps 1-5 with a strand of suture strand 542 already in place. Endoscope 500 can be moved to position suturing device 502 at a different location on tissue 598. Thus, suction or forceps from working channel 510 can be released. Suturing device 502 can be relocated along tissue 598 via an operator movement. Tissue 598 can be required by forceps or suction from working channel 510. Then, needle 552 can be rotated clock-wise by motor 503 to reacquire stop 544, push stop 544 through tissue 598 and redeposit stop 544 within socket 538 after forming a second loop of suture strand 542.

Terminating the suture can be accomplished via user technique to loop the ball and suture at the last thread to create a knot. The miniature forceps can have a cutting edge to cut the sutures.

FIG. 22 is a schematic end view of geared suturing device 600 used in conjunction with external working channel 602. Geared suturing device 600 can comprise pinion gear 604 that engages with outer gear teeth of ring gear 606 that directly drives suturing element 608. Geared suturing device 600 can be used with scope 610, which can comprise shaft 612, working channel 614, suturing channel 616, imaging lens 618 and light emitter 620. FIG. 22 shows pinion gear 604 directly driving ring gear 606 via external teeth of ring gear 606. Suturing element 608 can comprise a needle, such as needle 552, and can be directly mounted to ring gear 606. However, the center of rotation of ring gear 606 can be offset from the center of shaft 612 of scope 610 to allow the suturing element to pass in front of external working channel 602. Mounting ring 524 (FIG. 15) can include sideways (e.g., radially) projecting flanges or features to support ring gear 606. In the example of FIG. 22, external working channel 602 can be used similarly as working channel 510 of FIGS. 21A-21F or suturing channel 512 of FIGS. 21A-21F.

FIG. 23 is a schematic end view of geared suturing device 650 used in conjunction with external working channel 652. Geared suturing device 650 can comprise pinion gear 654, ring gear 656 and offsetting gear 657. Geared suturing device 650 can be used with scope 660, which can comprise shaft 662, working channel 664, suturing channel 666, imaging lens 668 and light emitter 670. Outer gear teeth of pinion gear 654 can drive outer gear teeth of ring gear 656 to indirectly drive suturing element 658 through offsetting gear 657. Inner gear teeth of ring gear 656 can drive outer gear teeth of offsetting gear 657 to rotate suturing element 658.

The examples of FIGS. 22 and 23 can allow for attachment of suturing devices of the present disclosure to be attached to existing endoscopes without requiring the use of two working channels within the endoscope. As such, single working channel scopes can be used or a second working channel within the endoscope can be used to perform other procedures besides the suturing.

The suturing devices of the present disclosure can have many benefits. For example, the devices of the present disclosure can be simple and intuitive, can provide full thickness tissue closure (e.g., greater than 2 cm), can be easily attached and compatible with any endoscope, can have ease of use (e.g., a circular needle with robust needle electric or manual drive mechanism), can reduce procedure times, can be low cost (e.g., under $1,000), can be mechanically robust.

Figure 24:
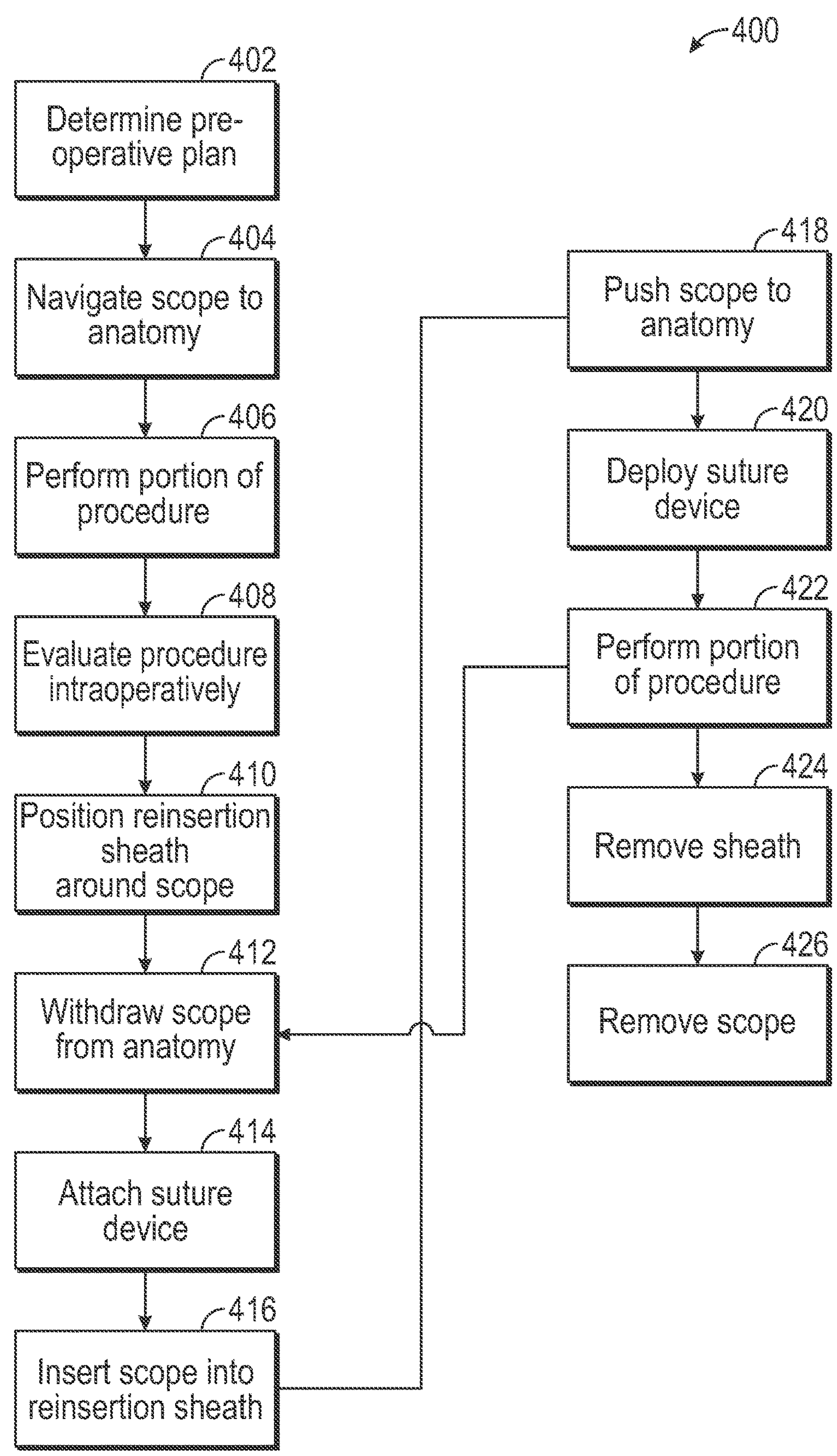
FIG. 24 is a block diagram illustrating methods of suturing tissuing using scopes, reinsertion sheaths and suturing attachments of the present disclosure.

FIG. 24 is a block diagram illustrating methods 400 of suturing issuing using scopes, reinsertion sheaths and suturing attachments of the present disclosure. Methods 400 can encompass the use of scope 102, reinsertion sheath 104, tissue separator device 106 and suturing device 108 of FIGS. 1 and 2, as well as any of the devices described herein, such as those of FIGS. 14-23.

At step 402, a patient can be evaluated for the performance of a medical procedure. In an example, it can be determined pre-operatively that the colon of the patient is to be treated with a tissue collector device, such as tissue separator device 106 (FIG. 1). The treatment can include the removal of diseased or other tissue. It can be determined preoperatively that the tissue can be collected without the need for incising, cutting or puncturing a duct wall of the patient. Thus, it can be determined preoperatively that the procedure will not involve suturing. The pre-operative plan can thus not involve attaching a suturing device, such as suturing device 108 (FIG. 1) to a scope to be used to perform the procedure, such as scope 102 (FIG. 1).

At step 404, a scope can be navigated through anatomy to the tissue of interest. An access portal or incision can be made in anatomy of the patient. In examples, scope 102 (FIG. 1) can be inserted into the patient and guided to a colon. Steering and navigation features of scope 102 can be employed to guide the distal end of scope 102 to target tissue. For example, imaging capabilities can be used to visualize anatomy including intersections of anatomical ducts. Steering capabilities can be used to turn the distal end of scope 102 into the desired duct and the target tissue within the desired duct.

At step 406, a portion of the medical procedure can be performed. For example, a portion of the procedure planned preoperatively at step 402 can be performed. Target tissue can be collected using tissue separator device 106. The target tissue can comprise tissue that is potentially diseased or otherwise indicative of a diseased condition of the patient. For example, separators 138A and 138B can be manipulated from control device 134 to engage target tissue one or more times to collect, separate if necessary, and store target tissue.

At step 408, the procedure being performed can be evaluated. For example, the total amount of tissue collected can be evaluated to see if a sufficient quantity has been collected. Also, the patient can be evaluated to determine if all of the diseased tissue has been collected. During the evaluation procedure, the anatomy of the patent can be reviewed to determine if any bleeding is occurring. If bleeding is occurring, it can be determined that a duct wall of the anatomy has been punctured. As such, it can be determined that an incision in the patient is to be closed, such as with a suturing device. Thus, it can be determined that scope 102 is to be withdrawn from the anatomy to facilitate insertion of a suturing device.

At step 410, a reinsertion sheath can be applied to scope 102 while scope 102 remains inserted into anatomy of the patient. As discussed herein, reinsertion sheath 104 can be manipulated to enlarge slit 126, such as by pulling end faces of flanges 128A and 128B (FIG. 7) apart in a circumferential direction. Thus, reinsertion sheath 104 can be moved radially over the proximal portion of shaft 110 (FIG. 2) of endoscope 102. Reinsertion sheath 104 can be relaxed to allow end faces of flanges 128A and 128B to be brought closer together. Additionally, reinsertion sheath 104 can be axially expanded to be inserted into the anatomy. For example, reinsertion sheath 104 can be converted from the compacted configuration of FIG. 8A to the expanded configuration of FIG. 8B in order to allow one of ends 150 or 152 (FIG. 6) to reach the target anatomy by being slid along scope 102. Reinsertion sheath 104 can be gently guided along shaft 110 to not impact the neighboring anatomy or features of scope 102. An axial closure mechanism, such as zipper closure mechanism 182 (FIG. 11) or interlocking rail closure mechanism 191 (FIGS. 12A and 12B), can be used to close slit 126. The axial closure mechanism can be employed before or during axial deployment of the reinsertion sheath.

At step 412, the scope can be withdrawn from the reinsertion sheath. For example, scope 102 can be withdrawn from the anatomy through reinsertion sheath 104. Reinsertion sheath 104 can remain in the anatomy to radially hold open a passage or tunnel to the target anatomy.

At step 414, an attachment can be coupled to the withdrawn scope. An attachment that has been decided to be used at step 408 can be assembled to the scope. For example, suturing device 108 can be attached to shaft 110 of scope 102. With reference to FIG. 15, mounting ring 524 can be positioned around distal end face 508 of shaft 506 of endoscope 500.

At step 416, the scope along with the attachment device can be inserted into the reinsertion sheath. Scope 102 with suturing device 108 can be slide into lumen 124 (FIG. 1) of reinsertion sheath 104.

At step 418, the scope can be pushed into the reinsertion sheath to reach the target anatomy. Scope 102 can be inserted until the distal end face and suturing device 108 reach the target anatomy at the distal end of reinsertion sheath 104.

At step 420, the attachment device assembled with the scope at step 414 can be deployed for use. For example, holder 546 can be locked into socket 538 to position stop 544 for use. Additionally, instrument 520 can be positioned in outlet 536 for used. Thus, in the pre-deployment stage, the size or shape of suturing device 502 can be made to have a smaller footprint to allow for easier insertion of scope 102 through reinsertion sheath 104. However, in the deployed position, suturing device 502 can configured for use, such as be extending instrumentation and components into engagement with suturing device 502.

At step 422, another portion of the surgical procedure planned at step 402 and evaluated at step 408 can be performed. For example, suturing device 108 can be used to close an incision and stop bleeding. Any of the various motor-driven suturing element described herein can be activated to provide a propulsion force to a suturing element to drive the suturing element. Furthermore, tissue separator device 106 can be used with scope 102 to remove additional tissue from the anatomy. Tissue separator device 106 can be inserted into lumen 119 (FIG. 1) and extended out the distal end of shaft 110 while suturing device 108 is attached thereto. Thus, separators 138A and 138B can be positioned proximate a suturing device for use.

Thereafter, method 400 can return to step 412, if desired, to remove the scope and the attachment device and reinsert the scope with a different reattachment device, or can continue to step 424 to complete the operation.

At step 424, the reinsertion sheath can be removed from the scope. For example, reinsertion sheath 104 can be slid proximally along shaft 110 of scope 102 until removed from the anatomy. Reinsertion sheath 104 can be opened at slit 126 to be pulled off of scope 102.

At step 426, the scope can be removed from the anatomy. For example, scope 102 can be pulled out of the anatomy. Alternatively, reinsertion sheath 104 and scope 102 can be removed together or scope 102 can be removed first and reinsertion sheath 104 removed second. Thereafter, the access portal in the patient can be appropriately closed.

As such, method 400 illustrates examples of methods of performing a medical procedure using a scope that can be withdrawn and reinserted into anatomy of a patient via an intraoperative reinsertion sheath that can be positioned around an in situ scope. The scope can be withdrawn intraoperatively to attach a supplemental device, such as the suturing devices disclosed herein, to perform intraoperatively determined ancillary procedures, such as suturing of an incision. As such, preoperative planning can be simplified because the need to decide a priori whether or not to use an ancillary device, such as a suturing attachment can be deferred to an intraoperative decision. The intraoperative change in procedure can be facilitated by the use of a reinsertion sheath that can be placed around a shaft of a scope already placed into anatomy of a patient, such as through the use of an axially extending slit extending along the reinsertion sheath. The intraoperative change in procedure can be facilitated by the use of a suturing device that can be easily and securely attached to the scope and changed from a stowed position that facilitates navigation of the scope to a deployed position that facilitates use of the suturing device with the scope. Thus, the devices and methods described herein can expedite medical procedures and facilitate better patient outcomes.

Various Notes & Examples

Example 1 is a suturing system for coupling to a scope having a scope shaft, the suturing system comprising: a drive shaft configured to extend along the scope shaft; a mounting ring configured to mount to a distal end of the scope shaft to receive the drive shaft; a pinion gear mounted to a distal end of the drive shaft; a ring gear rotatably mounted to the mounting ring in engagement with the pinion gear; and a needle mounted to the ring gear.

In Example 2, the subject matter of Example 1 optionally includes an electric motor connected to a proximal end of the drive shaft.

In Example 3, the subject matter of any one or more of Examples 1-2 optionally include a hand crank connected to a proximal end of the drive shaft.

In Example 4, the subject matter of any one or more of Examples 1-3 optionally include the scope shaft, wherein the scope shaft comprises a first working channel.

In Example 5, the subject matter of Example 4 optionally includes a suction device connected to the first working channel.

In Example 6, the subject matter of any one or more of Examples 4-5 optionally include a forceps positioned within the first working channel.

In Example 7, the subject matter of any one or more of Examples 4-6 optionally include a second working channel extending through the scope shaft through which the drive shaft extends.

In Example 8, the subject matter of Example 7 optionally includes wherein the pinion gear is mounted within the mounting ring.

In Example 9, the subject matter of any one or more of Examples 5-8 optionally include a tube defining a second working channel for the drive shaft, the tube extending alongside an exterior of the scope shaft.

In Example 10, the subject matter of any one or more of Examples 8-9 optionally include wherein the pinion gear is mounted outside the mounting ring.

In Example 11, the subject matter of any one or more of Examples 4-10 optionally include wherein the mounting ring further comprises an end plate having an opening configured to align with the first working channel to rotationally align the scope shaft and the mounting ring.

In Example 12, the subject matter of any one or more of Examples 1-11 optionally include wherein the mounting ring comprises an anchor catch configured to receive an anchor from a working channel.

In Example 13, the subject matter of Example 12 optionally includes wherein the anchor catch comprises a cylindrical body having an upper portion and a lower portion configured to hold an anchor and between which is disposed a pathway for the needle.

In Example 14, the subject matter of any one or more of Examples 12-13 optionally include wherein the needle comprises an anchor socket configured to receive the anchor form the anchor catch.

In Example 15, the subject matter of Example 14 optionally includes wherein the needle comprises a curved needle body extending from the ring gear toward a center of the scope shaft to align with the anchor catch.

In Example 16, the subject matter of any one or more of Examples 14-15 optionally include a suture tube extendable from the scope shaft.

In Example 17, the subject matter of Example 16 optionally includes a suturing anchor configured to seat in the anchor catch and the anchor socket, the suturing anchor connected to a strand of suture material extending from the suture tube.

In Example 18, the subject matter of Example 17 optionally includes wherein the suturing anchor comprises a ball.

In Example 19, the subject matter of any one or more of Examples 16-18 optionally include wherein the suture tube comprises an anchor holder configured to be inserted into the anchor catch.

In Example 20, the subject matter of any one or more of Examples 1-19 optionally include a retaining ring to hold the ring gear with the mounting ring, wherein the mounting ring comprises a seat upon which the mounting ring mounts to trap the ring gear between the retaining ring and the mounting ring.

Example 21 is a method comprising: coupling a suturing device to a distal end portion of a shaft of an endoscope; rotating a drive shaft extending along the shaft to the suturing device; rotating a suturing element with the drive shaft; moving the suturing element to grasp a suture anchor connected to suturing material; pulling the suturing material with the suturing element; bringing tissue into alignment with the suturing element; and pushing the suture anchor and the suturing material through the tissue.

In Example 22, the subject matter of Example 21 optionally includes rotating the drive shaft with an electric motor.

In Example 23, the subject matter of any one or more of Examples 21-22 optionally include rotating the drive shaft with a hand crank.

In Example 24, the subject matter of any one or more of Examples 21-23 optionally include bringing the tissue into alignment with the suturing element via suction.

In Example 25, the subject matter of any one or more of Examples 21-24 optionally include bringing the tissue into alignment with the suturing element via forceps.

In Example 26, the subject matter of any one or more of Examples 21-25 optionally include rotating a ring gear to which the suturing element is mounted centered on a distal end face of the shaft.

In Example 27, the subject matter of any one or more of Examples 21-26 optionally include rotating a ring gear to which the suturing element is mounted off-center of a distal end face of the shaft.

In Example 28, the subject matter of any one or more of Examples 21-27 optionally include rotating the suturing element with a pinion gear mounted to the drive shaft.

In Example 29, the subject matter of any one or more of Examples 21-28 optionally include rotating the suturing element with an offsetting gear driven by the drive shaft.

In Example 30, the subject matter of any one or more of Examples 21-29 optionally include reciprocating the suturing element with the drive shaft while moving the suturing device along the tissue.

In Example 31, the subject matter of any one or more of Examples 21-30 optionally include pulling the suturing material from the shaft of the endoscope.

In Example 32, the subject matter of any one or more of Examples 21-31 optionally include pulling the suturing material from alongside the shaft of the endoscope.

In Example 33, the subject matter of any one or more of Examples 21-32 optionally include holding the suture anchor in a receptacle of the suturing device; and removing the suture anchor from the receptacle with a socket in the suturing element.

In Example 34, the subject matter of any one or more of Examples 21-33 optionally include rotating the suturing element in a first direction from a home position to begin a suturing process.

In Example 35, the subject matter of Example 34 optionally includes rotating the suturing element in the first direction to pick-up the suture anchor from a socket of the suturing device mounted to the shaft.

In Example 36, the subject matter of Example 35 optionally includes rotating the suturing element in the first direction to pull the suturing material.

In Example 37, the subject matter of Example 36 optionally includes moving the endoscope to a first location on the tissue; and rotating the suturing element in the first direction to push the suture anchor through the first location on the tissue.

In Example 38, the subject matter of Example 37 optionally includes depositing the suture anchor in the socket.

In Example 39, the subject matter of Example 38 optionally includes rotating the suturing element in a second direction opposite the first direction to withdraw the suturing element from the tissue leaving the suture anchor in the socket.

In Example 40, the subject matter of Example 39 optionally includes moving the endoscope to a second location on the tissue and reengaging the suturing element to push the suture anchor through the second location.

Example 41 is a system for endoscopic suturing comprising: a scope shaft comprising a proximal end portion and a distal end face; an electric motor coupled to the scope shaft at the proximal end portion; a drive shaft extending from the electric motor to proximate the distal end face; a suturing element movably mounted to the scope shaft to move distal of the distal end face; and a gear system connecting the drive shaft and the suturing element; wherein the gear system is configured to convert rotational movement of the drive shaft into a suturing stroke of the suturing element.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times.

Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A suturing system for coupling to a scope having a scope shaft, the suturing system comprising:

a drive shaft configured to extend along the scope shaft, the drive shaft configured to rotate;

a mounting ring configured to mount to a distal end of the scope shaft to receive the drive shaft, the mounting ring comprising:

an annular body defining an opening to allow features of an end face of an endoscope access through the mounting ring; and a socket configured to receive a stop from a working channel of the scope shaft when the suturing system is coupled to the scope shaft;

a pinion gear mounted to a distal end of the drive shaft;

a ring gear rotatably mounted to the mounting ring in engagement with the pinion gear, wherein the pinion gear is configured to rotate the ring gear about the mounting ring when the drive shaft is rotated; and a needle mounted to the ring gear, the needle shaped to receive the stop from the socket.

2. The suturing system of claim 1, further comprising an electric motor connected to a proximal end of the drive shaft.

3. The suturing system of claim 1, further comprising a hand crank connected to a proximal end of the drive shaft.

4. The suturing system of claim 1, further comprising the scope shaft, wherein the scope shaft comprises a first working channel.

5. The suturing system of claim 4, further comprising a suction device connected to the first working channel.

6. The suturing system of claim 5, further comprising a tube defining a second working channel for the drive shaft, the tube extending alongside an exterior of the scope shaft.

7. The suturing system of claim 6, wherein the pinion gear is mounted outside the mounting ring.

8. The suturing system of claim 4, further comprising a forceps positioned within the first working channel.

9. The suturing system of claim 4, further comprising a second working channel extending through the scope shaft through which the drive shaft extends.

10. The suturing system of claim 4, wherein the mounting ring further comprises an end plate having an opening configured to align with the first working channel to rotationally align the scope shaft and the mounting ring.

11. The suturing system of claim 1, wherein:

the drive shaft is configured to extend along an exterior of the scope shaft; and the pinion gear is mounted within the mounting ring.

12. The suturing system of claim 1, wherein the socket comprises a cylindrical body having an upper portion and a lower portion configured to hold a stop and between which is disposed a pathway for the needle.

13. The suturing system of claim 1, wherein the needle comprises an anchor socket configured to receive the stop from the socket of the mounting ring.

14. The suturing system of claim 13, wherein the needle comprises a curved needle body extending along a helical path from the ring gear toward a center of the scope shaft to align with the socket in the circumferential direction relative to a central axis of the mounting ring.

15. The suturing system of claim 13, further comprising a suture tube extendable from the scope shaft.

16. The suturing system of claim 15, further comprising:

a stop configured to seat in the socket and the anchor socket, the stop connected to a strand of suture material extending from the suture tube.

17. The suturing system of claim 15, wherein the suture tube comprises an anchor holder configured to be inserted into the socket of the mounting ring.

18. The suturing system of claim 1, further comprising a retaining ring to hold the ring gear with the mounting ring, wherein the mounting ring comprises a seat upon which the mounting ring mounts to trap the ring gear between the retaining ring and the mounting ring.

19. A system for endoscopic suturing comprising:

a scope shaft extending along a central longitudinal axis, the scope shaft comprising a proximal end portion and a distal end face, wherein the distal end face comprises a working channel and an imaging lens;

an electric motor coupled to the scope shaft at the proximal end portion;

a drive shaft extending along an exterior of the scope shaft from the electric motor to proximate the distal end face;

a mounting ring configured to attach to the distal end face of the scope shaft, the mounting ring comprising:

an opening to allow the imaging lens to view through the mounting ring; and a socket for receiving a suture stop from the working channel of the scope shaft;

a suturing element movably mounted to the mounting ring to move distal of the distal end face, the suturing element comprising a helically shaped needle having a tip socket configured to hold a suture stop; and a gear system connecting the drive shaft and the suturing element;

wherein the gear system is configured to convert rotational movement of the drive shaft into a rotational suturing stroke of the suturing element so that the suturing element can receive the suture stop from the socket.

* * * * *